US010435568B2

(12) United States Patent
Denton et al.

(10) Patent No.: US 10,435,568 B2
(45) Date of Patent: Oct. 8, 2019

(54) SWITCHABLE ANTIFOULING COATINGS AND USES THEREOF

(71) Applicant: SANDIA CORPORATION, Albuquerque, NM (US)

(72) Inventors: Michele L. Baca Denton, Bosque, NM (US); Shawn M. Dirk, Albuquerque, NM (US); Ross Stefan Johnson, Wilmington, DE (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 245 days.

(21) Appl. No.: 15/407,164

(22) Filed: Jan. 16, 2017

(65) Prior Publication Data
US 2017/0226350 A1    Aug. 10, 2017

Related U.S. Application Data

(63) Continuation of application No. 14/455,702, filed on Aug. 8, 2014, now Pat. No. 9,580,608.

(51) Int. Cl.
C09D 183/08 (2006.01)
C09D 5/16 (2006.01)
A01N 31/04 (2006.01)
A01N 43/10 (2006.01)
A01N 55/02 (2006.01)
B05D 3/06 (2006.01)
C09D 165/02 (2006.01)

(52) U.S. Cl.
CPC ........... C09D 5/1637 (2013.01); A01N 31/04 (2013.01); A01N 43/10 (2013.01); A01N 55/02 (2013.01); B05D 3/065 (2013.01); C09D 5/1693 (2013.01); C09D 165/02 (2013.01); C09D 183/08 (2013.01)

(58) Field of Classification Search
CPC .. C09D 5/1637; C09D 5/1693; C09D 165/02; C09D 183/008
See application file for complete search history.

(56) References Cited

U.S. PATENT DOCUMENTS

| | | | | |
|---|---|---|---|---|
| 3,817,739 A * | 6/1974 | Abbott | ...................... | C02F 1/50 504/153 |
| 4,528,118 A * | 7/1985 | Murase | ...................... | C08F 8/00 252/500 |
| 4,818,797 A * | 4/1989 | Tsuda | ................... | C09D 5/1637 525/329.2 |
| 5,019,173 A * | 5/1991 | Gettings | ............... | C09D 5/1625 134/4 |
| 5,064,572 A * | 11/1991 | Ohnishi | .................. | C08G 61/02 252/500 |
| 5,302,192 A * | 4/1994 | McLearie | ............ | C09D 5/1668 106/15.05 |
| 7,314,505 B1 | 1/2008 | Wheeler et al. | | |
| 7,550,071 B1 | 6/2009 | Dirk et al. | | |
| 7,955,945 B1 | 6/2011 | Dirk et al. | | |
| 8,223,472 B1 | 7/2012 | Dirk et al. | | |
| 8,426,321 B1 | 4/2013 | Dirk et al. | | |
| 8,427,809 B1 | 4/2013 | Dirk et al. | | |
| 8,703,391 B1 | 4/2014 | Dirk et al. | | |
| 2004/0138331 A1* | 7/2004 | Lines | ...................... | C08F 20/34 523/122 |
| 2005/0260509 A1* | 11/2005 | West | ..................... | B41C 1/1041 430/12 |
| 2006/0062981 A1* | 3/2006 | Wallach | ................. | B82Y 30/00 428/215 |
| 2010/0204357 A1* | 8/2010 | Chasser | ................... | C09D 7/61 523/122 |

OTHER PUBLICATIONS

Banerjee, I. et al., "Antifouling Coatings: Recent Developments in the Design of Surfaces That Prevent Fouling by Proteins, Bacteria, and Marine Organisms," Adv. Mater. (2011) pp. 690-718, 23.

Burn, P.L. et al., "Precursor Route Chemistry and Electronic Properties of Poly(p-phenylene-vinylene), Poly[(2,5-dimethyl-p-phenylene)vinylene] and Poly [(2,5-dimethoxy-p-phenylene)vinylene]," J. Chem. Soc. Perkin (1992) pp. 3225-3231, Trans. 1.

Charnley, M. et al., "Designed polymer structures with antifouling-antimicrobial properties," Reactive Funct. Polym. (2011) pp. 329-334, 71.

Cheng, G. et al., "A Switchable Biocompatible Polymer Surface with Self-Sterilizing and Nonfouling Capabilities," Angew. Chem. Int. Ed. (2008) pp. 8831-8834, 47.

Dafforn, K.A. et al., "Antifouling strategies: History and regulation, ecological impacts and mitigation," Marine Pollut. Bull. (2011) pp. 453-465, 62.

Eshet, I. et al., "Chemical and Physical Factors in Design of Antibiofouling Polymer Coatings," Biomacromolecules (2011) pp. 2681-2685, 12.

Graham, M.V. et al., "Development of antifouling surfaces to reduce bacterial attachment," Soft Matter (2013) pp. 6235-6244, 9.

Johnson, R.S. et al., "Thermally Induced Failure of Polymer Dielectrics," Adv. Mater. (2010) pp. 1750-1753, 22.

Johnson, R.S. et al., "Photopatterning poly(p-phenylenevinylene) from xanthate precursor polymers," Chem. Commun. (2011) pp. 3936-3938, 47.

Johnson, R.S. et al., "Photolithographic patterning of alkoxy substituted poly(p-phenylenevinylene)s from xanthate precursors," J. Mater. Chem. C (2013) pp. 1428-1433, 1.

(Continued)

Primary Examiner — Margaret G Moore
(74) Attorney, Agent, or Firm — Helen S. Baca

(57) ABSTRACT

The present invention relates to antifouling coatings capable of being switched by using heat or ultraviolet light. Prior to switching, the coating includes an onium cation component having antimicrobial and antibacterial properties. Upon switching, the coating is converted to a conjugated polymer state, and the cationic component is released with any adsorbed biofilm layer. Thus, the coatings herein have switchable and releasable properties. Methods of making and using such coatings are also described.

20 Claims, 18 Drawing Sheets

(56) References Cited

OTHER PUBLICATIONS

Johnson, R.S. et al., "Thermally-Activated Pentanol Delivery from Precursor Poly(p-phenylenevinylene)s for MEMS Lubrication," Macromol. Rapid Commun. (2012) pp. 1346-1350, 33.

Kanazawa, A. et al., "Novel Polycationic Biocides: Synthesis and Antibacterial Activity of Polymeric Phosphonium Salts," J. Polym. Sci. Part A: Polym. Chem. (1993) pp. 335-343, 31.

Kanazawa, A. et al., "Antibacterial Activity of Polymeric Sulfonium Salts," J. Polym. Sci. Part A: Polym. Chem. (1993) pp. 2873-2876, 31.

Kuroki, H. et al., "Stimuli-Responsive Materials with Self-Healing Antifouling Surface via 3D Polymer Grafting," Adv. Funct. Mater. (2013) pp. 4593-4600, 23.

Li, M. et al., "Surface Modification of Silicone for Biomedical Applications Requiring Long-Term Antibacterial, Antifouling, and Hemocompatible Properties," Langmuir (2012) pp. 16408-16422, 28.

Liu, Y. et al., "Surface Structures of PDMS Incorporated with Quaternary Ammonium Salts Designed for Antibiofouling and Fouling Release Applications," Langmuir (2013) pp. 2897-2905, 29.

Magin, C.M. et al., "Non-toxic antifouling strategies," Mater. Today (2010) pp. 36-44, 13:4.

Majumdar, P. et al., "Combinatorial Materials Research Applied to the Development of New Surface Coatings XV: An Investigation of Polysiloxane Anti-Fouling/Fouling-Release Coatings Containing Tethered Quaternary Ammonium Salt Groups," ACS Comb. Sci. (2011) pp. 298-309, 13.

McBain, A.J. et al., "Effects of Quaternary-Ammonium-Based Formulations on Bacterial Community Dynamics and Antimicrobial Susceptibility," Appl. Environ. Microbiol. (2004) pp. 3449-3456, 70:6.

Pant, R.R. et al., "Synthesis and Biocidal Efficacy of Self-Spreading Polydimethylsiloxane Oligomers Possessing Oxyethylene-Functionalized Quaternary Ammoniums," J. Appl. Polym. Sci. (2009) pp. 2397-2403, 113.

Pranzetti, A. et al., "An Electrically Reversible Switchable Surface to Control and Study Early Bacterial Adhesion Dynamics in Real-Time," Adv. Mater. (2013) pp. 2181-2185, 25.

Salta, M. et al., "Assessment of marine biofilm attachment and growth for antifouling surfaces under static and controlled hydrodynamic conditions," Mater. Res. Soc. Symp. Proc. (2011) pp. 1-7, 1356.

Salta, M. et al., "Marine biofilms on artificial surfaces: structure and dynamics," Environ. Microbiol. (2013) pp. 2879-2893, 15:11.

Siedenbiedel, F. and Tiller, J.C., "Antimicrobial Polymers in Solution and on Surfaces: Overview and Functional Principles," Polymers (2012) pp. 46-71, 4.

Sundaram, H.S. et al., "Effect of Amphiphilic Structures on Antifouling and Fouling Release Properties of PS-B-P(E/B)-B-Pi Based Triblock Copolymer," Polymer (2011) pp. 1034-1035, 52(2).

Tu, Q. et al., "Antifouling properties of poly(dimethylsiloxane) surfaces modified with quaternized poly(dimethylaminoethyl methacrylate)," Colloid. Surf. B: Bionterfaces (2013) pp. 361-370, 102.

Wessling, R.A., "The Polymerization of Xylylene Bisdialkyl Sulfonium Salts," J. Polym. Sci.: Polym. Symp. (1985) pp. 55-66, 72.

Xie, L. et al., "Coatings with a self-generating hydrogel surface for antifouling," Polymer (2011) pp. 3738-3744, 52.

Xue, L. et al., "Bio-inspired self-cleaning PAAS hydrogel released coating for marine antifouling," J. Colloid Interface Sci. (2014) pp. 178-183, 421.

Zhao, X. et al., "Hierarchically engineered membrane surfaces with superior antifouling and self-cleaning properties" J. Membr. Sci. (2013) pp. 93-101, 441.

\* cited by examiner

SWITCHABLE ANTIFOULING COATINGS AND USES THEREOF

CROSS-REFERENCE TO RELATED APPLICATION

This application is a continuation of prior application Ser. No. 14/455,702, filed Aug. 8, 2014, which is hereby incorporated by reference in its entirety and which is now U.S. Pat. No. 9,580,608.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to an antifouling coating having releasable and switchable properties. In particular, these coatings can be switched by exposure to heat or ultraviolet light. Methods of making and using such coatings are also described herein.

BACKGROUND OF THE INVENTION

Biofouling is the accumulation of microorganisms, plants, algae, or animals on wetted surfaces. Marine biofouling begins with the adhesion of a conditioning film of proteins and polysaccharides within minutes of submerging an artificial surface in seawater. Within a day, bacteria and single cell diatoms can attach to the conditioning film, initiating the formation of a biofilm. Within weeks, colonizers, such as algal spores, barnacle cyprids, and marine fungi, become attached to the biofilm to form a thick coating. Such biofouling increases the weight, hydrodynamic friction, and corrosion of shipping vessels and other marine systems (see, e.g., Majumdar P et al., "Combinatorial materials research applied to the development of new surface coatings XV: an investigation of polysiloxane anti-fouling/fouling-release coatings containing tethered quaternary ammonium salt groups," *ACS Comb. Sci.* 2011; 13:298-309.

For example, marine hydrokinetic (MHK) technologies harness the energy of water as it moves and are vital in providing clean and sustainable energy. Biofouling presents an ongoing problem for MHKs as water organisms cling to their surfaces, resulting in a decrease in operation efficiency. Development of effective antifouling coatings to facilitate easy removal of organisms, or prevent adhesion, would ensure MHKs continue to operate at optimal efficiency over time.

Historically, antifouling coatings have been used to prevent or delay the biofouling accumulation. Traditional commercial coatings have included biocides comprising chemical substances incorporated into an antifouling surface coating that deter or kill the microorganisms responsible for formation of the biofilm. The most common biocides are tributyltin (TBT), leachable cuprous oxide, and self-polishing copolymers with alkyl silane functional monomers. However, these biocides are persistent toxins to larger aquatic organisms and are being phased out. In addition, low-toxicity fouling release and antifoulants, such as polysiloxane and quaternary ammonium salts have also been investigated. The hydrophobic polysiloxanes prevent adhesion of larger microorganisms and enable the release of fouling organisms at high speed, but have problems with mechanical strength and long term stability.

Many of these coatings rely on ammonium salts that are amphoteric surfactants (see, e.g., McBain A J et al., "Effects of quaternary-ammonium-based formulations on bacterial community dynamics and antimicrobial susceptibility," *Appl. Environ. Microbiol.* 2004; 70(6):3449-59). The antimicrobial and antibacterial mode of action of the quaternary ammonium salts has been described for ammonium salts that contain a long chain aliphatic moiety which can penetrate a cell wall leading to lysis (Hugo W B, "The mode of action of antibacterial agents," *J. Appl. Bacteriol.* 1967; 30(1):17-50). Ammonium-based coatings have been used for greater than 50 years due in part to their broad spectrum antimicrobial activity (see, e.g., Pant R R et al., "Synthesis and biocidal efficacy of self-spreading polydimethylsiloxane oligomers possessing oxyethylene-functionalized quaternary ammoniums," *J. Appl. Polym. Sci.* 2009; 113:2397-403). Benzalkonium chlorides have been increasingly used as additives in disinfectant cleaning formulations.

Current estimates indicate that the total US anti-microbial market will reach close to $1 billion by the year 2015 (see, e.g., "Anti-microbial Coatings: A US Market Report" (Global Industry Analysts, Inc., 2011). As the market size increases, there is a real need for the development of novel high performance antimicrobial and antibacterial coatings. Furthermore, some organisms have become resistant to the ammonium-based antimicrobials and antibacterials, necessitating the need for alternative coating methodologies (Heir E et al., "Resistance to quaternary ammonium compounds in *Staphylococcus* spp. isolated from the food industry and nucleotide sequence of the resistance plasmid pST827," *J. Appl. Bacteriol.* 1995 August; 79(2):149-56).

One of the largest problems of current coatings is that fact that they are not long lived because additional microorganisms eventually colonize the remains of the cells that were lysed initially by the antifouling coatings. Therefore, a need remains for an alternative type of antifouling coating capable of facilitating the removal of the dead organisms and accumulated biofilm.

SUMMARY OF THE INVENTION

Accordingly, the present invention relates to antifouling coatings having releasable and switchable properties.

In one aspect, the invention features an antifouling coating having releasable and switchable properties, the coating including an onium cation (e.g., a sulfonium cation, an ammonium cation, an oxonium cation, a diazonium cation, a halonium cation, or a phosphonium cation) covalently attached to an alpha carbon of a polymer, where the coating is configured to release the cation upon thermal or photochemical treatment.

In some embodiments, the polymer includes one or more hydrogens covalently attached to a beta carbon that is adjacent to the alpha carbon.

In some embodiments, upon thermal or photochemical treatment, the coating is configured to release a fouling release layer including the cation and to maintain a polymerized layer on a surface, where the polymerized layer includes a conjugated form of the polymer.

In other embodiments, the polymer includes a polyphenylene backbone and/or a polysiloxane backbone. In further embodiments, a polymerized layer on a surface includes a conjugated form of the polyphenylene backbone or the polysiloxane backbone.

In some embodiments, the polymer has a structure of:

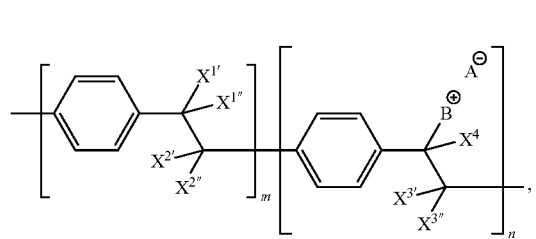
(I)

where each of $X^{1'}$, $X^{1''}$, $X^{2'}$, $X^{2''}$, $X^{3'}$, $X^{3''}$, and $X^4$ is, independently, selected from the group consisting of H, optionally substituted $C_{1-6}$ alkyl, optionally substituted $C_{2-6}$ alkenyl, and halo; B is an onium cation; A is an anion; m is an integer of from 0 to 1000; and n is an integer of from 1 to 1000. In further embodiments, at least one of $X^{3'}$ and $X^{3''}$ is H.

In some embodiments, the polymer has the structure of:

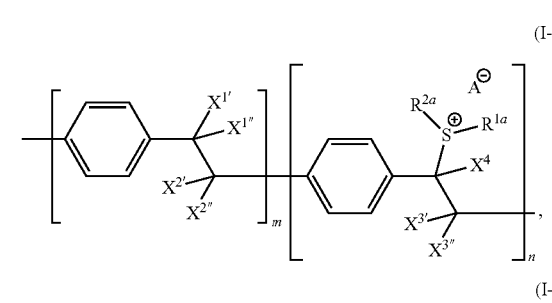
(I-A)

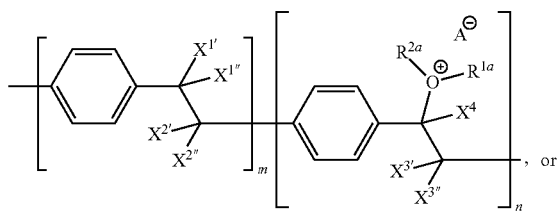
(I-B)

or

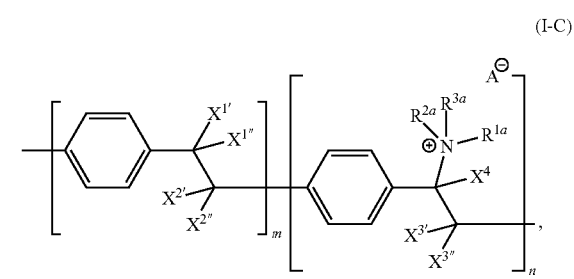
(I-C)

where each of $R^{1a}$, $R^{2a}$, and $R^{3a}$, if present, is, independently, H, optionally substituted $C_{1-24}$ alkyl, or optionally substituted $C_{2-24}$ alkenyl (e.g., optionally substituted $C_{2-6}$ alkenyl); or where two of $R^{1a}$, $R^{2a}$, and $R^{3a}$, taken together with the heteroatom to which each are attached, form an optionally substituted heterocycle; or where $R^{1a}$ and $R^{2a}$, taken together, includes an optionally substituted $C_{2-12}$ alkylene or an optionally substituted $C_{2-12}$ heteroalkylene.

In other embodiments, the polymer has a structure of:

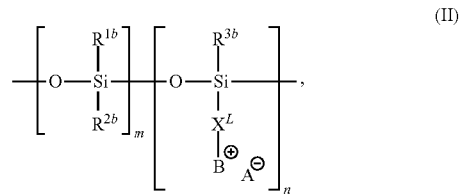
(II)

where each of $R^{1b}$, $R^{2b}$, and $R^{3b}$ is, independently, selected from the group consisting of H, hydroxyl, optionally substituted $C_{1-6}$ alkyl, optionally substituted $C_{2-6}$ alkenyl, optionally substituted $C_{1-6}$ alkoxy, and halo; $X^L$ is optionally substituted $C_{1-16}$ alkylene or optionally substituted $C_{1-12}$ heteroalkylene; B is an onium cation; A is an anion; m is an integer of from 0 to 1000; and n is an integer of from 1 to 1000.

In other embodiments, the polymer has a structure of:

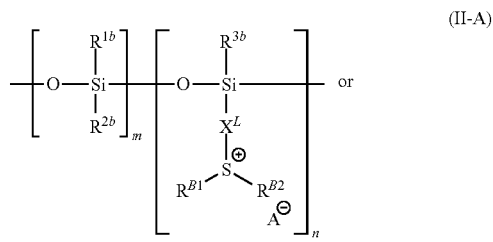
(II-A)

or

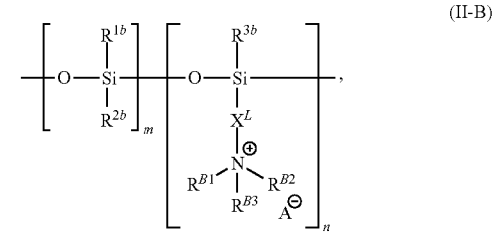
(II-B)

where each of $R^{B1}$, $R^{B2}$, and $R^{B3}$, if present, is, independently, H, optionally substituted $C_{1-24}$ alkyl, or optionally substituted $C_{2-24}$ alkenyl (e.g., optionally substituted $C_{2-6}$ alkenyl); or where $R^{B1}$ and $R^{B2}$, taken together with the sulfur atom to which each are attached, form an optionally substituted heterocycle; or where $R^{B1}$ and $R^{B2}$, taken together, includes an optionally substituted $C_{2-12}$ alkylene or an optionally substituted $C_{2-12}$ heteroalkylene; or where two or more of $R^{B1}$, $R^{B2}$, and $R^{B3}$, taken together with the nitrogen atom to which each are attached, form an optionally substituted heterocycle; or where $R^{B1}$ and $R^{B2}$, taken together, includes an optionally substituted $C_{2-12}$ alkylene or an optionally substituted $C_{2-12}$ heteroalkylene;

In another aspect, the invention features a substrate including an antifouling coating having releasable and switchable properties on a surface thereof, where the coating includes an onium cation covalently attached to an alpha carbon of a polymer and where the coating is configured to release the cation upon thermal or photochemical treatment.

In some embodiments, the polymer includes one or more hydrogens covalently attached to a beta carbon that is adjacent to the alpha carbon. In some embodiments, upon thermal or photochemical treatment, the coating is configured to release a fouling release layer including the cation and to maintain a polymerized layer on the substrate, where the polymerized layer includes a conjugated form of the polymer. In other embodiments, the substrate further includes a primer layer disposed between the coating and the surface of the substrate.

In yet another aspect, the invention features a method of treating a marine surface, the method including applying a first antifouling coating having releasable and switchable properties on the marine surface, or a portion thereof, where the coating includes an onium cation covalently attached to an alpha carbon of a polymer; and treating the first coating with heat or ultraviolet light to release the cation, thereby maintaining a polymerized layer on the marine surface, where the polymerized layer includes a conjugated form of the polymer.

In some embodiments, the method further includes treating the polymerized layer with one or more onium cation precursors to generate a second antifouling coating on the marine surface.

In any embodiment herein, the coating includes an onium cation covalently attached to an alpha carbon of a polymer, where the coating is configured to release the cation upon thermal or photochemical treatment.

In any embodiment herein, the antifouling coating includes a polycationic sulfonium containing polymer as a demand switchable antibiofouling coating. The sulfonium group is linked at the benzylic position of a poly(phenylene vinylene) (PPV) precursor polymer. The polymer can be switched to a conjugated polymer with heat or ultraviolet (UV) light. As the coating is converted to the conjugated PPV state, the coating exhibits a volume change, shrinking the coating by as much as 65%. The volume change combined with the low surface adhesion of the biofilm to the remaining PPV results in the removal of the attached biofilm.

Definitions

As used herein, the term "about" means+/−10% of any recited value. As used herein, this term modifies any recited value, range of values, or endpoints of one or more ranges.

By "alkenyl" is meant an optionally substituted $C_{2-24}$ alkyl group having one or more double bonds. The alkenyl group can be cyclic (e.g., $C_{3-24}$ cycloalkenyl) or acyclic. The alkenyl group can also be substituted or unsubstituted. For example, the alkenyl group can be substituted with one or more groups including, but not limited to, alkyl (e.g., any described herein), cycloalkyl, alkoxy, amino, carboxyl (—C(O)OH), ether, halo, hydroxyl, nitro, silyl, sulfo-oxo, or thiol.

By "alkoxy" is meant —OR, where R is an optionally substituted alkyl group, as described herein. Exemplary alkoxy groups include methoxy, ethoxy, butoxy, trihaloalkoxy, such as trifluoromethoxy, etc. The alkoxy group can also be substituted or unsubstituted. For example, the alkoxy group can be substituted with one or more groups including, but not limited to, alkyl (e.g., any described herein), cycloalkyl, alkoxy, amino, carboxyl (—C(O)OH), ether, halo, hydroxyl, nitro, silyl, sulfo-oxo, or thiol.

By "alkyl" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one or more groups including, but not limited to, alkyl, alkenyl, alkynyl, cycloalkyl, alkoxy, amino, carboxyl (—C(O)OH), ether, halo, hydroxyl, nitro, silyl, sulfo-oxo, or thiol. The alkyl group can be a primary, secondary, or tertiary alkyl group substituted with one or more substituents (e.g., one or more halo or alkoxy). In some embodiments, the alkyl group is a $C_{1-3}$, $C_{1-6}$, $C_{1-12}$, $C_{1-16}$, $C_{1-18}$, $C_{1-20}$, or $C_{1-24}$ alkyl group.

By "alkylene" is meant a divalent form of an alkyl group, as described herein. Exemplary alkylene groups include methylene, ethylene, propylene, butylene, etc. In some embodiments, the alkylene group is a $C_{1-3}$, $C_{1-6}$, $C_{1-12}$, $C_{1-16}$, $C_{1-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ alkylene group. The alkylene group can be branched or unbranched. The alkylene group can also be substituted or unsubstituted. For example, the alkylene group can be substituted with one or more groups including, but not limited to, alkyl, alkenyl, alkynyl, cycloalkyl, alkoxy, amino, carboxyl (—C(O)OH), ether, halo, hydroxyl, nitro, silyl, sulfo-oxo, or thiol.

By "alkynyl" is meant an optionally substituted $C_{2-24}$ alkyl group having one or more triple bonds. The alkynyl group can be cyclic or acyclic. The alkynyl group can also be substituted or unsubstituted. For example, the alkynyl group can be substituted with one or more groups including, but not limited to, alkyl (e.g., any described herein), cycloalkyl, alkoxy, amino, carboxyl (—C(O)OH), ether, halo, hydroxyl, nitro, silyl, sulfo-oxo, or thiol.

By "amino" is meant —$NR^{N1}R^{N2}$, where each of $R^{N1}$ and $R^{N2}$ is, independently, H or optionally substituted alkyl, or $R^{N1}$ and $R^{N2}$, taken together with the nitrogen atom to which each are attached, form a heterocycle.

By "ammonium" is meant a group including a protonated nitrogen atom $N^+$. Exemplary ammonium groups include —$N^{\oplus}R^{N1}R^{N2}R^{N3}$, where each of $R^{N1}$, $R^{N2}$, and $R^{N3}$ is, independently, H or optionally substituted alkyl; or $R^{N1}$ and $R^{N2}$, taken together with the nitrogen atom to which each are attached, form a heterocycle; or $R^{N1}$ and $R^{N2}$, taken together, form an optionally substituted alkylene or heteroalkylene (e.g., as described herein).

By "anion" is meant a monoatomic or polyatomic species having one or more elementary charges of the electron. Exemplary, non-limiting anions include a halide (e.g., $F^-$, $Cl^-$, $Br^-$, or $I^-$), a hydroxide (e.g., $OH^-$), a borate (e.g., tetrafluoroborate ($BF_4^-$), a carbonate (e.g., $CO_3^{2-}$ or $HCO_3^-$), or a sulfate (e.g., $SO_4^{2-}$).

By "aryl" is meant a group that contains any carbon-based aromatic group including, but not limited to, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl (e.g., haloalkyl, such as any described herein), halo, cycloalkyl, alkoxy, alkenyl, cycloalkenyl, alkynyl, cycloalkynyl, aryl, heteroaryl, aldehyde, amino, carboxyl (—C(O)OH), ester, ether, halo, hydroxyl, ketone, azide, nitro, silyl, sulfo-oxo, or thiol.

By "diazonium" is meant a group including —$N_2^+$.

By "halo" is meant F, Cl, Br, or I.

By "haloalkyl" is mean an alkyl group, as defined herein, substituted with one or more halo.

By "halonium" is meant a group including —X$^+$, where X is halo as defined herein. Exemplary halonium groups include an iodonium group (e.g., —I$^+$), a bromonium group (e.g., —Br$^+$), a chloronium group (e.g., —Cl$^{+-}$), or a fluoronium group (e.g., —F$^+$).

By "heteroalkylene" is meant a divalent form of an alkylene group, as defined herein, containing one, two, three, or four non-carbon heteroatoms (e.g., independently selected from the group consisting of nitrogen, oxygen, phosphorous, sulfur, or halo).

By "heterocycle" is meant a 5-, 6- or 7-membered ring, unless otherwise specified, containing one, two, three, or four non-carbon heteroatoms (e.g., independently selected from the group consisting of nitrogen, oxygen, phosphorous, sulfur, or halo). The 5-membered ring has zero to two double bonds and the 6- and 7-membered rings have zero to three double bonds. The term "heterocycle" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring and another monocyclic heterocyclic ring, such as indolyl, quinolyl, isoquinolyl, tetrahydroquinolyl, benzofuryl, benzothienyl and the like. Heterocyclics include thiiranyl, thietanyl, tetrahydrothienyl, thianyl, thiepanyl, aziridinyl, azetidinyl, pyrrolidinyl, piperidinyl, azepanyl, pyrrolyl, pyrrolinyl, pyrazolyl, pyrazolinyl, pyrazolidinyl, imidazolyl, imidazolinyl, imidazolidinyl, pyridyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like.

By "hydroxyl" is meant —OH.

By "oxonium" is meant a group including a protonated oxygen atom O$^+$. Exemplary oxonium groups include —O$^+$R$^{O1}$R$^{O2}$, where each of R$^{O1}$ and R$^{O2}$ is, independently, H, optionally substituted alkyl, optionally substituted alkenyl, or optionally substituted aryl; or wherein R$^{O1}$ and R$^{O2}$, taken together, form an optionally substituted alkylene or heteroalkylene (e.g., as described herein).

By "phosphonium" is meant a group including a protonated phosphorous atom P$^+$. Exemplary phosphonium groups include —P$^+$R$^{P1}$R$^{P2}$R$^{P3}$, where each of R$^{P1}$, R$^{P2}$, and R$^{P3}$ is, independently, H, optionally substituted alkyl, optionally substituted alkenyl, or optionally substituted aryl; or wherein two of R$^{P1}$, R$^{P2}$, and R$^{P3}$, taken together, form an optionally substituted alkylene or heteroalkylene (e.g., as described herein).

By "siloxane" is meant a group including —SiO— or capable of forming —SiO— groups. The siloxane group can be cyclic or acyclic. The siloxane group can include —Si(OR$^{Si}$)$_3$, where each R$^{Si}$ is, independently, H or an optionally substituted alkyl group (e.g., any described herein); or can include —Si(R$^{Si'}$)$_3$ where each R$^{Si'}$ is independently H, optionally substituted alkyl, or halo. The siloxane group can also be substituted or unsubstituted. For example, the siloxane group can be substituted with one or more groups including, but not limited to, alkyl (e.g., any described herein), cycloalkyl, alkoxy, amino, carboxyl (—C(O)OH), ether, halo, hydroxyl, nitro, silyl, sulfo-oxo, or thiol.

By "sulfonium" is meant a group including a protonated sulfur atom S$^+$. Exemplary sulfonium groups include —S$^+$R$^{S1}$R$^{S2}$, where each of R$^{S1}$ and R$^{S2}$ is, independently, H, optionally substituted alkyl, or optionally substituted alkenyl; or R$^{S1}$ and R$^{S2}$, taken together with the sulfur atom to which each are attached, form a heterocycle; or R$^{S1}$ and R$^{S2}$, taken together, form an optionally substituted alkylene or heteroalkylene (e.g., as described herein).

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

DETAILED DESCRIPTION OF THE INVENTION

Figure 1A:
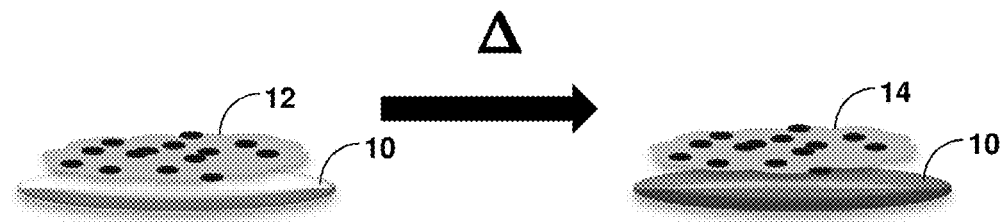
FIG. 1A-1C shows an exemplary coating of the invention. Provided are (A) a schematic showing a surface 10 having an antifouling coating; (B) a schematic showing the first antifouling coating 120 on a substrate 150; and (C) a schematic showing a poly (phenylene vinylene) (PPV)-based conjugated polymer on a substrate 250.

The present invention relates to releasable and switchable coatings. For instance, the coating is releasable because a portion of the coating can be released from a surface. As shown in FIG. 1A, when a coating accumulates biofilm 12 on the surface 10, exposure of the coating to heat results in release of a portion of the coating and any biofilm 14 attached to that released coating.

In addition, the coating is switchable because an external stimulus (e.g., heat or ultraviolet light, e.g., light of from about 100 nm to 400 nm) is required to convert the coating from a first polymeric structure (e.g., including cations) into a second polymeric structure (e.g., lacking such cations but having a conjugated structure). For instance, the coating of the invention can include a polymer having a backbone and one or more pendant groups having onium cations. In particular, the polymer is configured to undergo an elimination reaction, thereby cleaving the onium cation upon exposure to a stimulus. Thus, the first polymeric structure includes both the backbone and onium cations, and the second polymeric structure includes a conjugated structure arising from the elimination reaction but lacks the cations.

Figure 1B:
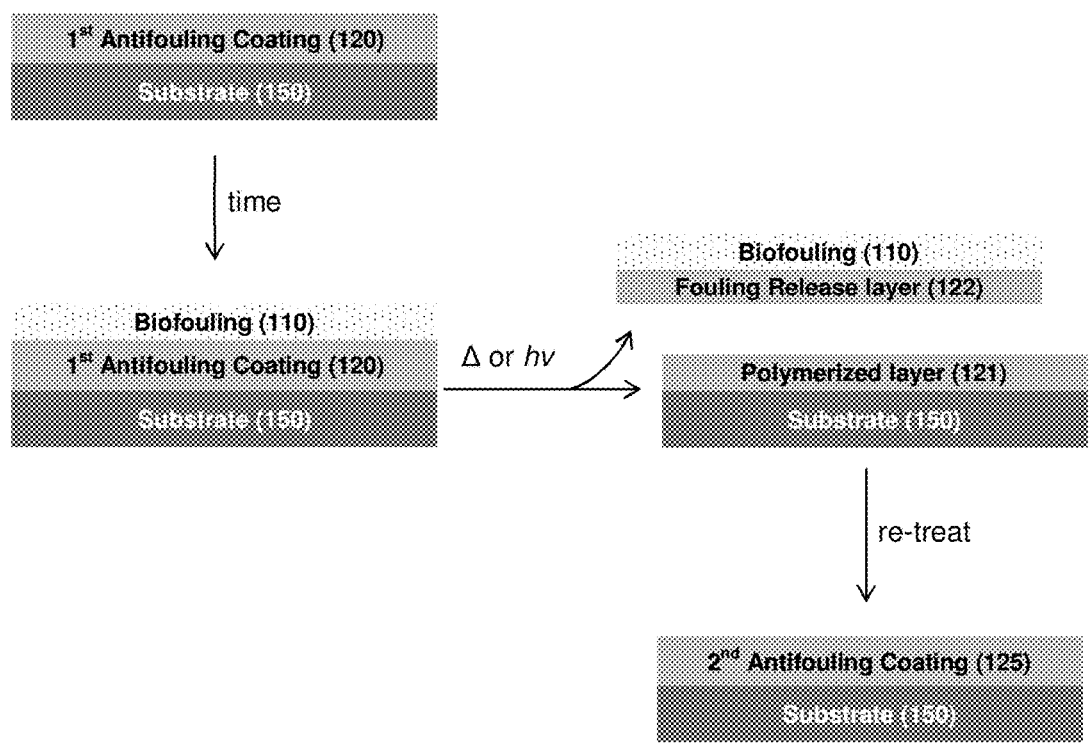

FIG. 1B shows an exemplary releasable and switchable coating. As can the seen, the coating 120 is disposed on the substrate 150. Over time, a biofouling film 110 forms on the coating 120. Upon being switched by heat (Δ) or photoactivation (hυ), the coating 120 is released from the substrate 150 in the form of a fouling release layer 122 that lifts the biofouling film 110 away from the substrate. Remaining on the substrate is a polymerized layer 121, which includes the conjugated form of the polymer that initially formed the coating. In some embodiments, the polymerized layer 121 can be re-treated to form a second antifouling coating 125 on the substrate.

Figure 1C:
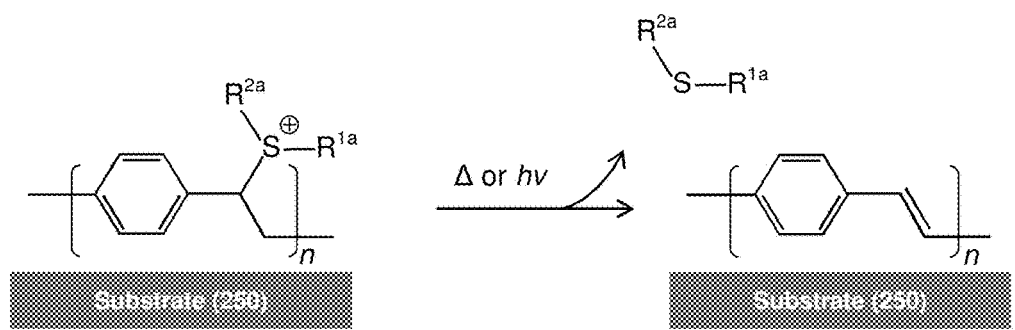

FIG. 1C shows an exemplary polymer having a backbone and one or more pendant groups having an onium cation (i.e., a sulfonium-based cation). Prior to switching, the coating includes a sulfonium ($—S^{\oplus}R^{1a}R^{2a}$). Upon switching, the sulfonium-based component ($SR^{1a}R^{2a}$) of the coating is released as part of the fouling release layer, and the polymerized component (poly(phenylene vinylene)) is maintained as a polymerized layer on the surface of the substrate 250. As described herein, the invention encompasses polymers having other backbones and/or other onium cation groups.

In particular embodiments, the switchable coating provides an antimicrobial surface prior to switching and a nonfouling surface after switching. Such a coating would be beneficial to release adhered bacterial cells. In addition, the switching properties can be further tuned. For instance, one or more leaving groups on the polymer can be chosen in order to promote elimination and subsequent formation of the conjugated alkene bond in the polymerized layer.

Described herein are polymers for such coatings, as well as methods of making and using such coatings.

Polymers of Formulas (I) and (II)

Figure 2A:
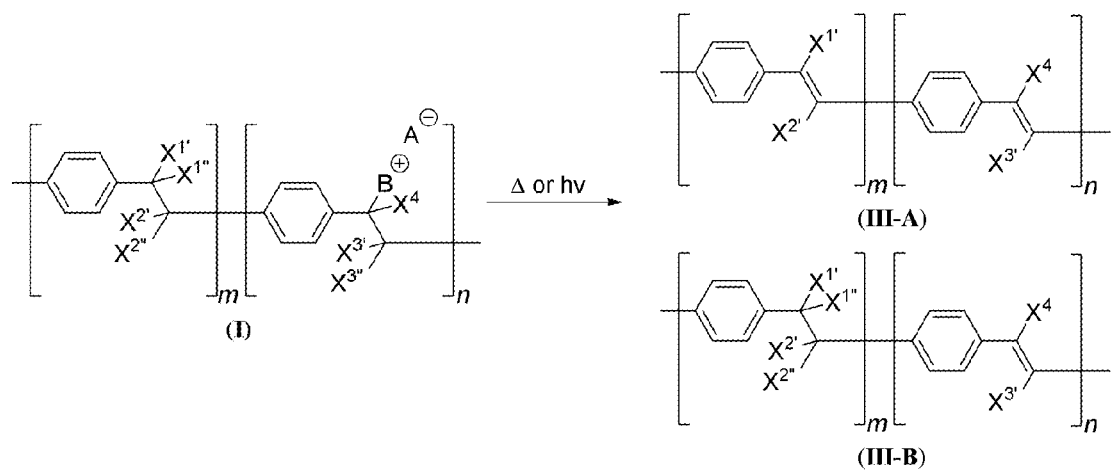
FIG. 2A-2D shows exemplary PPV-based polymers for an antifouling coating. Provided are (A) an exemplary generic structure before (I) and after thermal or photochemical switching (III-A, III-B); (B) exemplary PPV-based polymers (I-A), (I-B), and (I-C); (C) exemplary PPV-based polymers (I-1) and (I-2); and (D) exemplary PPV-based copolymers (I-3) and (I-4).
Figure 2B:
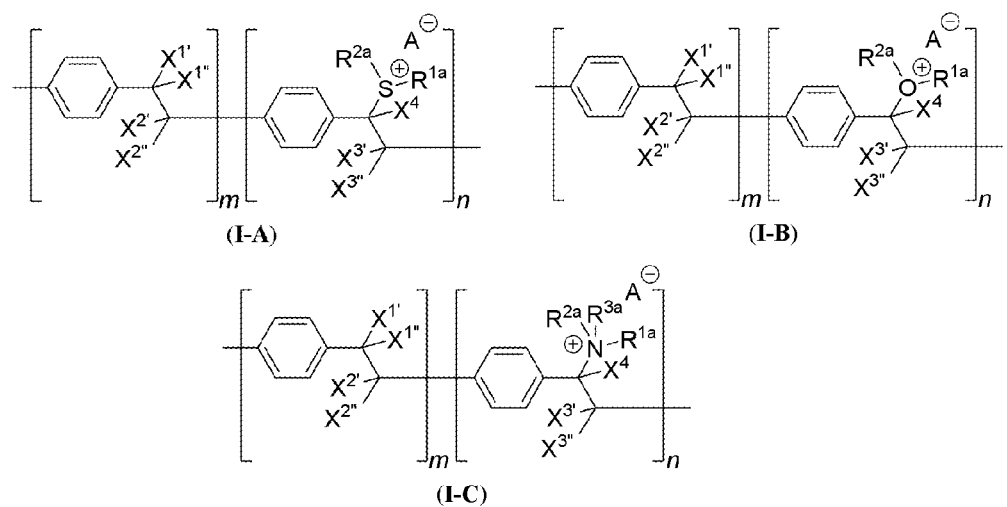
Figure 2C:
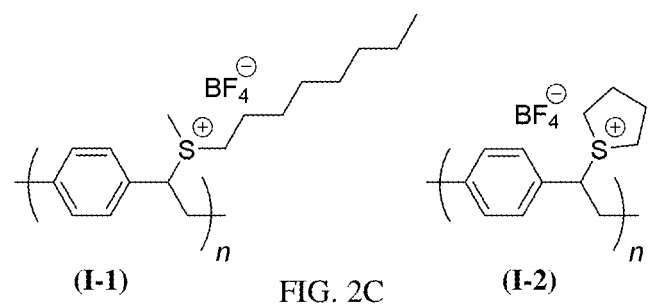
Figure 2D:
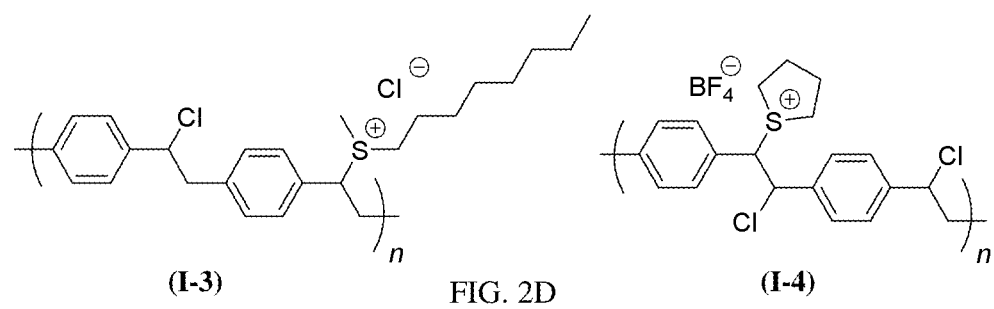

The present invention encompasses polymers having formulas (I) and (II):

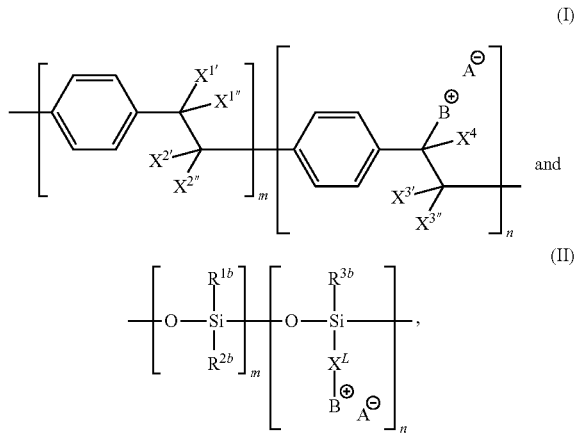

where each of $R^{1b}$, $R^{2b}$, $R^{3b}$, $X^{1'}$, $X^{1''}$, $X^{2'}$, $X^{2''}$, $X^{3'}$, $X^{3''}$, $X^4$, $X^L$, A, B, m, and n are as described herein. Polymer (I) encompasses PPV-based polymers (e.g., generic polymers (I-A), (I-B), and (I-C) in FIG. 2B), such as polymers (I-1) and (I-2) (FIG. 2C) and copolymers (I-3) and (I-4) (FIG. 2D). Polymer (II) encompasses siloxane-based polymers, such as those having a sulfonium cation (e.g., polymers (II-A) and (II-1) in FIGS. 5B and 5C) and those having an ammonium cation (e.g., polymers (II-B), (II-2), (II-3), and (II-4) in FIGS. 5B and 5D).

As can be seen, the polymers of the invention include an onium cation $B^+$. $B^+$ includes any onium cation useful for preparing a biocidal, antimicrobial and/or antifouling coating. Exemplary onium cations $B^\oplus$ include a sulfonium cation (e.g., —$S^+R^{1a}R^{1b}$ or —$S+R^{S1}R^{S2}$), an ammonium cation (e.g., —$N^+R^{1a}R^{2a}R^{3a}$ or —$N^\oplus R^{N1}R^{N2}R^{N3}$) an oxonium cation (e.g., —$O^+R^{1a}R^{1b}$ or —$O^+R^{O1}R^{O2}$), a diazonium cation (—$N_2^+$), a halonium cation (—$X^+$), or a phosphonium cation (e.g., —$P^+R^{1a}R^{1b}R^{1c}$ or —$P^+R^{P1}R^{P2}R^{P3}$), where exemplary R groups are described herein. Exemplary precursor agents B to synthesize such onium cations are also described herein.

Figure 5A:
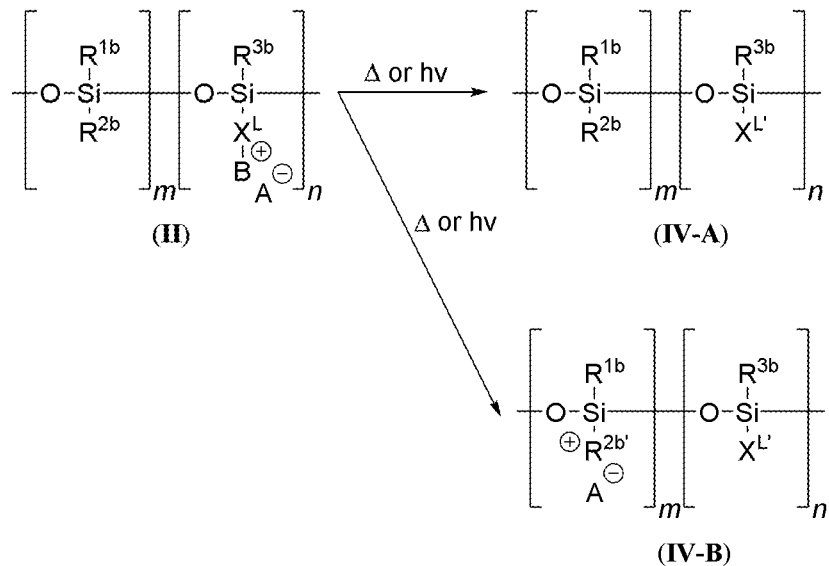
FIG. 5A-5D shows exemplary siloxane-based polymers for an antifouling coating. Provided are (A) an exemplary generic structure before (II) and after thermal or photochemical switching (IV-A, IV-B); (B) exemplary generic structures (II-A) and (II-B); (C) exemplary siloxane-based polymers having a sulfonium cation (II-1) or an ammonium cation (II-2); and (D) exemplary siloxane-based copolymers having an ammonium cation (II-3) and (II-4).
Figure 5B:
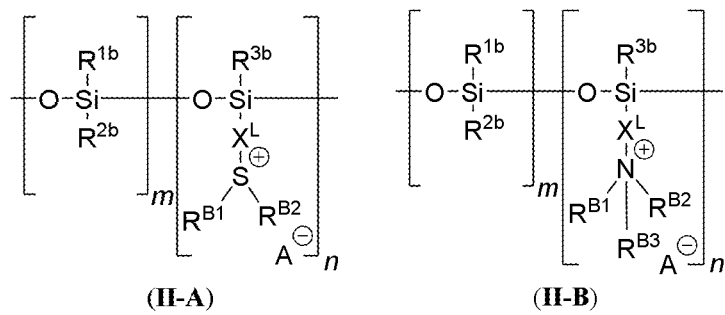
Figure 5C:
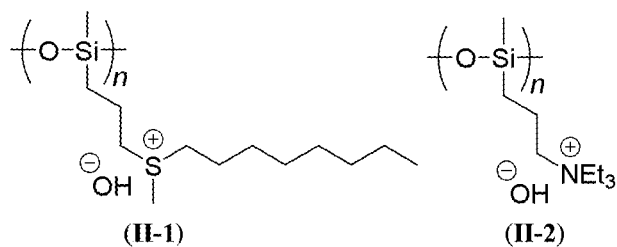
Figure 5D:
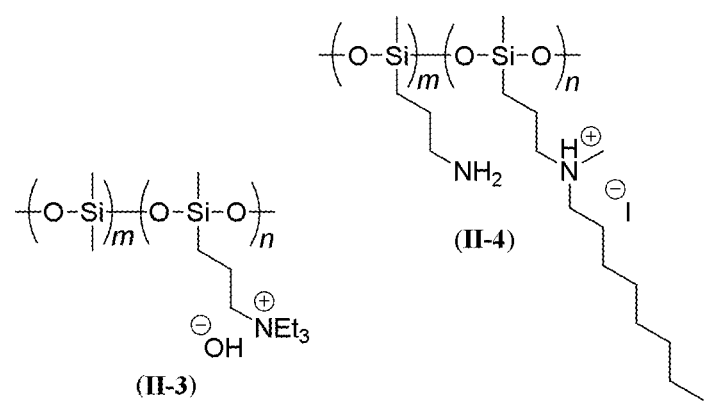

In particular, the polymers and coatings of the invention are configured to be switchable. For instance, FIG. 2A shows polymer (I) capable of being switched, thereby forming conjugated polymers (III-A) and/or (III-B). In another instance, FIG. 5A shows polymer (II) being switched to form conjugated polymer (IV-A) and/or (IV-B).

Switching of the polymer can be conducted using heat or photoactivation. For instance, thermal conditions include exposure to heat (e.g., more than about 120° C., e.g., between about 120° C. to 250° C.). In another instance, photoactivation conditions include exposure to ultraviolet light (e.g., between about 280 nm to 320 nm).

The polymers of the invention can be synthesized using any useful procedure (e.g., any described herein). Unless otherwise noted, R, L, X, A, and/or B groups include any described herein.

SCHEME I

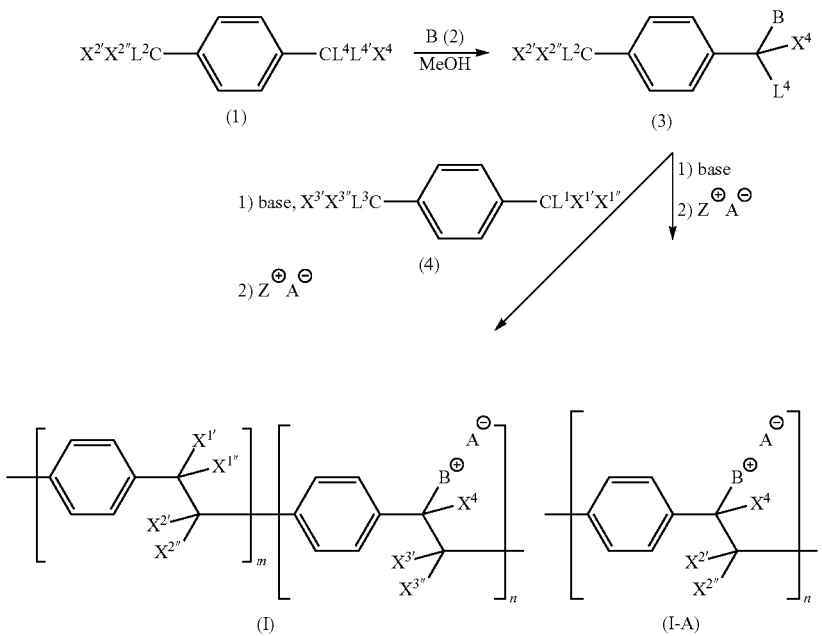

In one embodiment, the PPV-based polymer is synthesized according to Scheme I. As can be seen, compound (1) is an aryl-based reactant, where each of $L^2$, $L^4$, and $L^{4'}$ is, independently, H or a leaving group (e.g., any described herein); and each of $X^{2'}$, $X^{2''}$, and $X^4$ is independently, H, halo, optionally substituted alkyl, optionally substituted alkenyl, or a leaving group (e.g., any described herein). The phenyl ring of compound (1) is optionally substituted (e.g., with any group provided herein for an aryl group).

Compound (1) is reacted with an onium precursor agent B (2) in a solvent (e.g., a polar solvent, such as a polar protic solvent, e.g., MeOH) to form polymer precursor (3) having a sulfonium cation. Optionally, sulfide agent (2) reacts with both benzylic carbons on compound (1), thereby forming a precursor where one of $X^{2'}$, $X^{2''}$, or $L^2$ is $-S^+R^{1a}R^{2a}$.

The onium precursor agent can be any useful agent. For example, for a sulfonium cation, the precursor onium agent can be a sulfide agent $SR^{1a}R^{2a}$, thereby providing polymer (I-A). In another example, for an oxonium cation, the precursor onium agent can be an alcohol agent $R^{1a}OH$ or an ether agent $R^{1a}OR^{1b}$, thereby providing polymer (II-B). In yet another example, for an ammonium cation, the precursor onium agent can be an ammonia agent $NR^{1a}R^{2a}R^{3a}$ thereby providing polymer (II-B). Other precursor agents and onium are described herein, and a skilled artisan would understand that such oniums are encompassed by polymer (I).

In one embodiment, precursor (3) is polymerized with monomer (4) to a form copolymer, and an anion exchange reaction is performed with ZA to provide copolymer (I). In some embodiments, each of $L^1$ and $L^3$ is, independently, H or a leaving group (e.g., any described herein); and each of $X^{1'}$, $X^{1''}$, $X^{3'}$, and $X^{3''}$ is independently, H, halo, optionally substituted alkyl, optionally substituted alkenyl, or a leaving group (e.g., any described herein). In further embodiments, Z is an alkali cation (e.g., $Na^+$ or $K^+$) or an alkaline cation (e.g., $Mg^{2+}$, $Ca^{2+}$, or $Sr^{2+}$), and A is an anion (e.g., $Cl^-$, $Br^-$, $OH^-$, $BF_4^-$, $HCO_3^-$, or $SO_4^{2-}$). Alternatively, the anion exchange reaction includes the use of an oxidizing agent (e.g., $Ag_2O$ to provide anion $OH^-$).

In another embodiment, precursor (3) is polymerized without other monomers to form a polymer, and an anion exchange reaction is performed with ZA (e.g., any described herein) to provide polymer (I-A). Examples encompassed by Scheme I include those provided in FIGS. 3A, 3C, 4A, and 4B.

SCHEME II

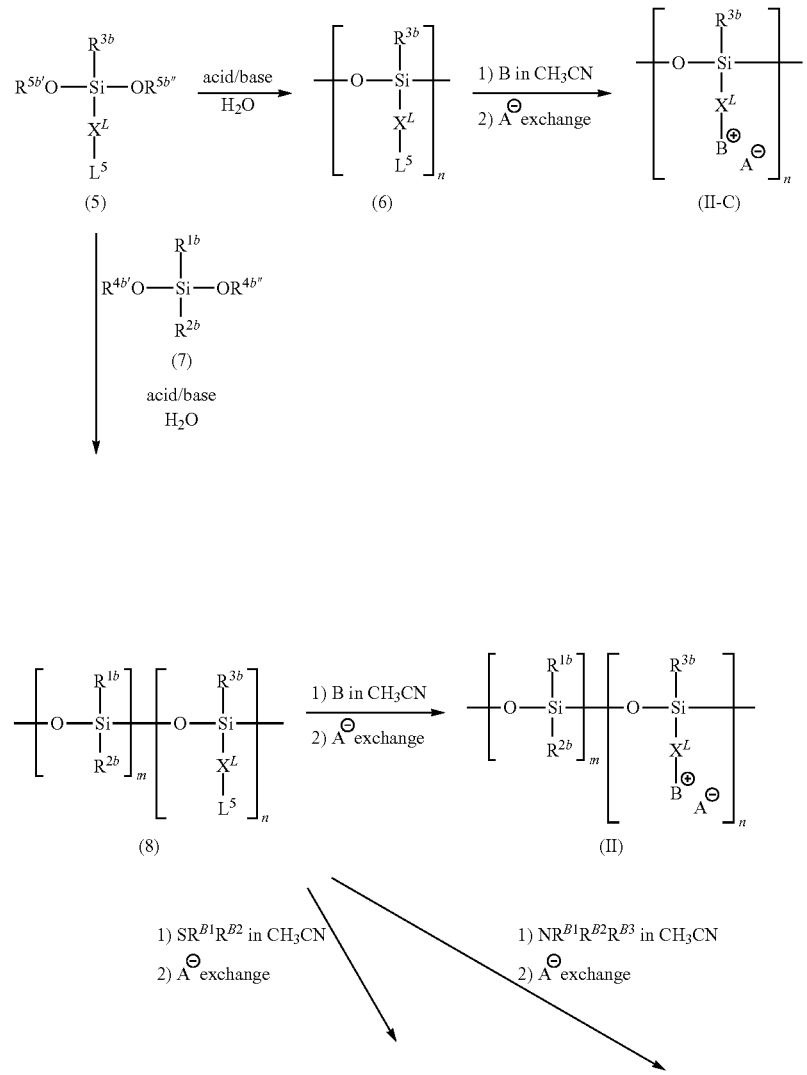

-continued

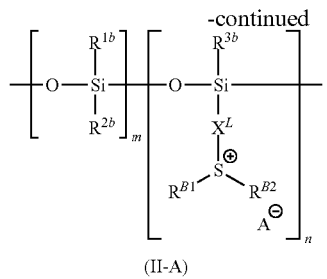

(II-A)

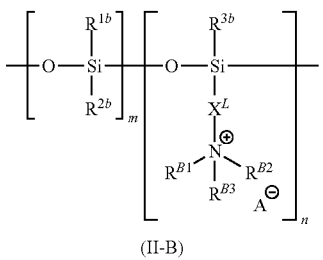

(II-B)

In one embodiment, the siloxane-based polymer is synthesized according to Scheme II. As can be seen, compound (5) is a siloxane monomer, where $L^5$ is H or a leaving group (e.g., any described herein); $X^L$ is a linker (e.g., any described herein); and each of $R^{3b}$, $R^{5b'}$, and $R^{5b''}$ is independently, H, optionally substituted alkyl, optionally substituted alkenyl, or a leaving group (e.g., any described herein).

In one embodiment, the siloxane monomer (5) is polymerized to form a siloxane polymer (6), which is then reacted with an onium precursor agent (B) in a solvent (e.g., any described herein). Next, an anion exchange reaction is performed with $A^-$ (e.g., with ZA, such as any described herein, or an oxidizing agent, e.g., $AgO_2$) to provide the cationic polymer (II-C). Exemplary onium precursor agents include a sulfide agent (e.g., $SR^{B1}R^{B2}$), an amine agent (e.g., $NR^{B1}R^{B2}R^{B3}$), an alcohol agent (e.g., $OR^{B1}R^{B2}$), an ether agent (e.g., $OR^{B1}R^{B2}$), a halide agent (e.g., $I_2$, $Br_2$, $Cl_2$, $F_2$, aryl halide, and alkyl halide, in optional combinations with organotrifluoroborates), a halonium ylide agent (e.g., a phenyliodonium ylide), a diazonium agent (e.g., $NH_2$ combined with $NO_2$), and/or a phosphine agent (e.g., $PR^{B1}R^{B2}R^{B3}$), where $R^{B1}$, $R^{B2}$, and $R^{B3}$ is, independently, any useful functional group (e.g., H, halo, optionally substituted $C_{1-24}$ alkyl, optionally substituted $C_{2-6}$ alkenyl, or optionally substituted aryl; or where $R^{B1}$ and $R^{B2}$, taken together with the heteroatom atom to which each are attached, form an optionally substituted heterocycle; or where $R^{B1}$ and $R^{B2}$, taken together, comprises an optionally substituted $C_{2-12}$ alkylene or an optionally substituted $C_{2-12}$ heteroalkylene).

In another embodiment, siloxane monomer (5) is polymerized in the presence of another monomer (7), where each of $R^{1b}$, $R^{2b}$, $R^{4b'}$, and $R^{4b''}$ is independently, H, hydroxyl, optionally substituted alkyl, optionally substituted alkenyl, optionally substituted alkoxy, halo, or a leaving group (e.g., any described herein), thereby forming a siloxane copolymer (8).

The copolymer (8) can be reacted with various onium precursor agents (B) in any useful solvent (e.g., a polar solvent, such as any described herein) and then reacted with $A^-$ (e.g., with ZA, such as any described herein) to provide the cationic copolymer (II).

In one embodiment, the onium precursor agent is a sulfide agent (e.g., $SR^{B1}R^{B2}$), thereby forming the siloxane-based sulfonium polymer (II-A). In another embodiment, the onium precursor agent is an amine agent (e.g. $NR^{B1}R^{B2}R^{B3}$) thereby forming the siloxane-based ammonium polymer (II-B).

Figure 6A:
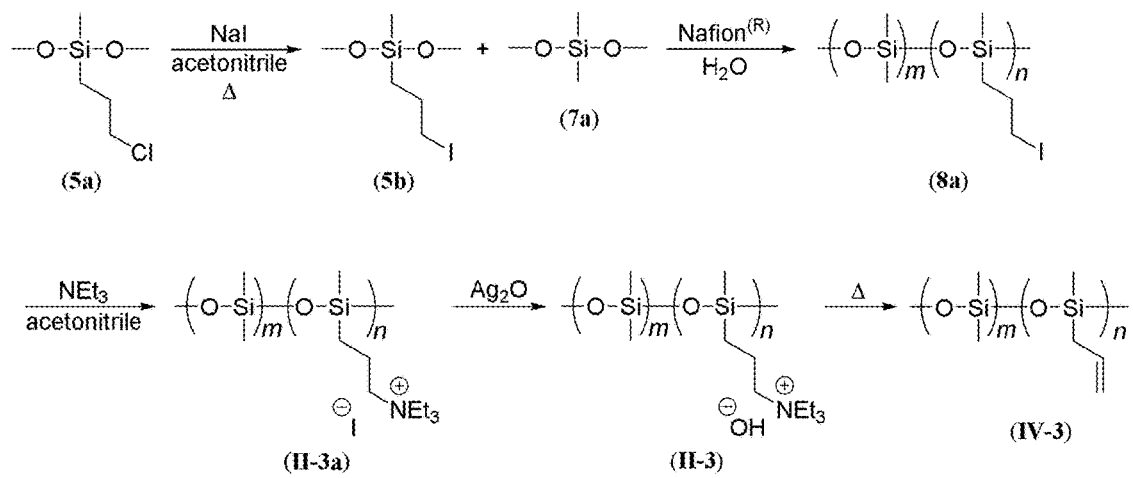
FIG. 6A-6D shows (A) a synthetic scheme for siloxane-based copolymer (II-3); (B) a synthetic scheme for siloxane-based generic structure (II-Ca) and (II-Cb); (C) a graph showing thermogravimetric analysis (TGA) for a siloxane-based polymer having a sulfonium cation (II-1); and (D) a TGA graph for a siloxane-based polymer having an ammonium cation (II-2).
Figure 6B:
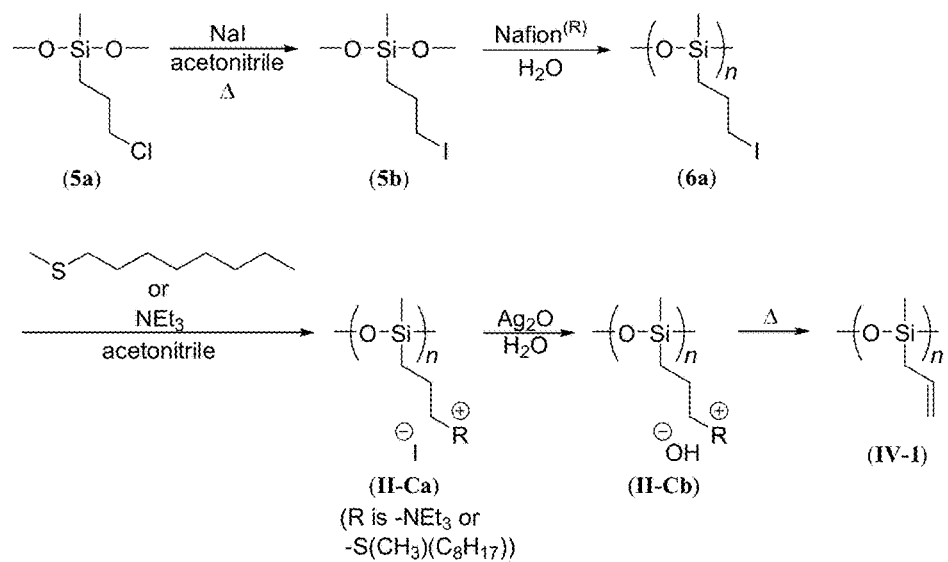

Examples encompassed by Scheme II include those provided in FIG. 6A-6B. FIG. 6A provides a synthetic scheme for siloxane-based copolymer (II-3) having an ammonium cation. FIG. 6B provides a synthetic scheme for siloxane-based polymers (II-Ca) and (II-Cb), which can include a sulfonium or an ammonium cation.

For any reaction herein, the polymerization reaction can be performed under any useful conditions. For instance, precursor (3) or (5) either with or without monomer (4) or (7) can be polymerized in the presence of a base (e.g., NaOH), an acid, a catalyst (e.g., Nafion®, which is a sulfonated tetrafluoroethylene based fluoropolymer-copolymer), and/or a membrane in a polar solvent or solvent system (e.g., acetone, dimethylformamide, acetonitrile, tetrahydrofuran, ethyl acetate, dimethyl sulfoxide, water, ethanol, methanol, isopropanol, or combinations thereof).

For any structure provided herein, the leaving group can be a chloride, a bromide, an iodide, a fluoride, an onium group (e.g., any described herein, such as sulfonium, ammonium, or oxonium), an ester, an xanthate, a nitrile, an amine, a nitro group, a carbonate, a dithiocarbamate, a sulfonium group, an oxonium group, an iodonium group, a pyridinium group, an ammonium group, a borate group, a borane group, a sulphinyl group, or a sulfonyl group, as well as protonated, alkylated, halogenated (e.g., triflate forms), or protected forms (e.g., tosylated or mesylated forms) of any of these. Methods of making and testing polymers are described in U.S. Pat. Nos. 7,955,945, 8,426,321, and 8,427,809, each of which is incorporated herein by reference in its entirety.

For any structure provided herein, the linker can be any group capable of participating in an elimination reaction that cleaves the onium component from the polymer. For instance, the linker can be an alkylene or heteroalkylene group having H on the beta carbon, thereby allowing the onium cation of the alpha carbon to leave.

Exemplary methods of synthesizing and characterizing polymers are described in Johnson R S et al., "Thermally induced failure of polymer dielectrics," Adv. Mater. 2010 April; 22(15):1750-3; Johnson R S et al., "Photopatterning poly(p-phenylenevinylene) from xanthate precursor polymers," Chem. Commun. (Camb.) 2011 Apr. 7; 47(13):3936-8; Burn P L et al., "Precursor route chemistry and electronic properties of poly(p-phenylenevinylene), poly[(2,5-dimethyl-p-phenylene)vinylene] and poly[(2,5-dimethoxy-p-phenylene)vinylene]," J. Chem. Soc. Perkins Trans. 1 1992; 23:3225-31; Johnson R S et al., "Thermally-activated pentanol delivery from precursor poly(p-phenylenevinylene)s for MEMS lubrication," Macromol. Rapid Commun. 2012 Aug. 28; 33(16):1346-50; Johnson R S et al., "Photolithographic patterning of alkoxy substituted poly(p-phenylenevinylene)s from xanthate precursors," J. Mater. Chem. C 2013; 1:1428-33; Kanazawa A et al., "Novel polycationic biocides: synthesis and antibacterial activity of polymeric phosphonium salts," J. Polym. Sci. Part A: Polym. Chem. 1993 October; 31:335-43; Kanazawa A et al., "Antibacterial activity of polymeric sulfonium salts," J. Polym. Sci. Part A: Polym. Chem. 1993 October; 31(11):2873-6; and Wessling R A, "The polymerization of xylylene bisdialkyl sulfonium salts," J. Polym. Sci.: Polym. Symp. 1985; 72:55-66, each of which is incorporated herein by reference in its entirety.

Modifications to Coatings

The coatings can include any additional modifications or components that would increase its antibiofouling characteristics and/or improve its release properties. Exemplary modifications include the addition of one or more antimicrobials or antibiotics (e.g., antimicrobial peptides), biocides (e.g., oxides of copper and zinc and isothiazolone), particles (e.g., nanoparticle, microspheres, or carriers, such as hydroxyapatite), enzymes (e.g., proteases), brush polymers, poly(ethylene glycol), etc. In addition, the coatings of the invention can be provided in any useful form, such as in a water-insoluble matrix (e.g., rosin).

Additional modifications are described in Banerjee I et al., "Antifouling coatings: recent developments in the design of surfaces that prevent fouling by proteins, bacteria, and marine organisms," *Adv. Mater.* 2011; 23:690-718; Charnley M et al., "Designed polymer structures with antifouling-antimicrobial properties," *Reactive & Functional Polym.* 2011; 71:329-34; Dafforn K A et al., "Antifouling strategies: history and regulation, ecological impacts and mitigation," *Marine Pollution Bulletin* 2011; 62:453-65; Salta M et al., "Assessment of marine biofilm attachment and growth for antifouling surfaces under static and controlled hydrodynamic conditions," *Mater. Res. Soc. Symp. Proc.* 2011; 1356: DOI: 10.1557/op1.2011.1139 (7 pages); Salta M et al., "Marine biofilms on artificial surfaces: structure and dynamics," *Environ. Microbiol.* 2013; 15(11):2879-93; Siedenbiedel F et al., "Antimicrobial polymers in solution and on surfaces: overview and functional principles," *Polymers* 2012; 4:46-71; and Tu Q et al., "Antifouling properties of poly(dimethylsiloxane) surfaces modified with quaternized poly(dimethylaminoethyl methacrylate)," *Colloids Surf B: Biointerfaces* 2013; 102:361-70, each of which is incorporated herein by reference in its entirety.

Surfaces

The antifouling coating can be used to coat any useful surface or substrate. Exemplary surfaces and substrates include metals (e.g., aluminum, stainless steel, galvanized steel, iron, etc.), glass, plastics (e.g., high-density polyethylene (HDPE), fiberglass, etc.), polymers, filters, and membranes (e.g., polysulfone membranes). The surface of any useful article can be coated. Exemplary surfaces include marine surfaces (e.g., surfaces on marine hydrokinetic devices, such as a powerbuoy, a wave attenuator, or a tidal turbine), water treatment membranes, marine devices, pipes, cooling towers, and medical devices. Marine surfaces include any surface that is in contact with fresh, salt, estuarine, brackish, sea, or other bodies of water including, for example, ship surfaces (e.g., ship hulls, boat hulls, submarine hulls, propellers, rudders, keels, centerboards, fins, hydrofoils), deck surfaces, antennae, aquatic constructions, barges, bells, bridges, buoys, cables, cooling system surfaces, cooling water intake or discharge pipes, cranes, depth charges, docks, dredges, fish preserving structures, fishing nets, floating beacons, floating breakwaters, gun barrels, gun mounts, jetties, ladders, launch tubes, mines, nautical beacons, periscopes, piers, pipelines, pipes, pipes, plumbs, pontoons, port facilities, pumps, ropes, seaside industrial plants, snorkels, tanks, torpedoes, transponders, turbines, valves, water pipes in power stations, wharves, wheels, and wires.

Additional surfaces include medical devices, catheters, biosensors, such as any described in Banerjee I et al., "Antifouling coatings: recent developments in the design of surfaces that prevent fouling by proteins, bacteria, and marine organisms," *Adv. Mater.* 2011; 23:690-718, which is incorporated herein by reference in its entirety.

The surface can optionally be modified with a primer and/or a siloxane polymer. Exemplary primers include an epoxy-based primer, a polyamide epoxy-based primer, a vinyl-based primer (e.g., Intertuf® 203, available from Akzo Nobel Chemicals, Pasadena, Calif.), a zinc-based primer (e.g., a zinc rich ethyl silicate primer, such as Interzinc® 22, available from Akzo Nobel Chemicals, Pasadena, Calif.), etc. Exemplary epoxy-based primers include a polymer of epoxy resin and bisphenol A, including commercially available forms (e.g., Intergard® 264 or Intertuf® 362 available from Akzo Nobel Chemicals, Pasadena, Calif.). Exemplary siloxane polymers include those formed from a trialkoxy siloxane, a trihalide siloxane, etc.

Furthermore, the surface can be treated or coated in any useful manner. For instance, the entire surface can be treated to include a uniform coating of the polymer (e.g., formulas (I) or (II)). In other embodiments, the surface can be heterogeneous, in which patterns of the polymer can be included.

Methods for Preparing and/or Testing Coatings

The coating can be prepared and tested by any useful method, as described below. Methods for preparing the coating include spray coating, painting, brushing, spin coating, casting, or dip coating the polymer (e.g., formula (I) or (II)) onto a surface, and then drying or curing the polymer.

The present invention encompasses optional use of a primed surface. In some instances, a primed surface allows for indirect or direct attachment of the coating of the invention. In particular, non-reactive surfaces (e.g., metals) can be activated by applying a primer. In other instances, the surface is not primed.

The coatings can be tested in any useful manner. In some embodiments, the method includes inoculating a coating with bacteria, incubating the coating with the bacteria, rinsing the coating (e.g., to remove non-adherent bacteria), optionally treating the coating with water under pressure, staining the coating to detect a biofilm (if present), and extracting and/or quantifying the stain.

In other embodiments, the method includes inoculating a coating with microalgae, incubating the coating with the microalgae, rinsing the coating (e.g., to remove non-adherent microalgae), optionally treating the coating with water under pressure, extracting and/or quantifying chlorophyll (e.g., such as measuring fluorescence).

The coatings can be tested by any useful technique. Exemplary techniques include surface spectroscopy methods, such as X-ray photoelectron spectroscopy (XPS), atomic force microscopy (AFM), or scanning electron microscopy (SEM); surface energy measurement techniques, such as tensiometry or measurement of contact angles; as well as algal and or bacterial assays, including inoculation of surfaces with algal or bacterial samples, measurement of settled or adhered spores or cells, exposure of inoculated surfaces to shear forces, and/or visualization of biomass by fluorescence or optical methods.

Additional methods for preparing and/or testing coatings are provided in Graham M V et al., "Development of antifouling surfaces to reduce bacterial attachment," *Soft Matter* 2013; 9:6235-44; Kuroki H et al., "Stimuli-responsive materials with self-healing antifouling surface via 3D polymer grafting," *Adv. Funct. Mater.* 2013; 23:4593-600; Li M et al, "Surface modification of silicone for biomedical applications requiring long-term antibacterial, antifouling, and hemocompatible properties," *Langmuir* 2012; 28:16408-22; Liu Y et al., "Surface structures of PDMS incorporated with quaternary ammonium salts designed for antibiofouling and fouling release applications," *Langmuir*

2013; 29:2897-905; Majumdar P et al., "Combinatorial materials research applied to the development of new surface coatings XV: an investigation of polysiloxane antifouling/fouling-release coatings containing tethered quaternary ammonium salt groups," *ACS Comb. Sci.* 2011 May 9; 13(3):298-309; Pant R R et al., "Synthesis and biocidal efficacy of self-spreading polydimethylsiloxane oligomers possessing oxyethylene-functionalized quaternary ammoniums," *J. Appl. Polym. Sci.* 2009; 113:2397-403; Pranzetti A et al., "An electrically reversible switchable surface to control and study early bacterial adhesion dynamics in real-time," *Adv. Mater.* 2013; 25:2181-5; Xie L et al., "Coatings with a self-generating hydrogel surface for antifouling," *Polymer* 2011; 52:3738-44; Xue L et al., "Bio-inspired self-cleaning PAAS hydrogel released coating for marine antifouling," *J. Colloid Interface Sci.* 2014; 421:178-83; and Zhao X et al., "Hierarchically engineered membrane surfaces with superior antifouling and self-cleaning properties," *J. Membr. Sci.* 2013; 441:93-101, each of which is incorporated by reference in its entirety.

Uses

The present invention can be adapted for many uses, including, without limitation, e.g., on marine surfaces for marine hydrokinetic devices (e.g., a powerbuoy, a wave attenuator, or a tidal turbine), water treatment membranes, marine devices, pipes, cooling towers, as well as on medical devices. Other surfaces include those on biomedical devices, biosensors, etc.

In particular, biofouling in marine applications occur over various different time scales and length scales. For instance, different time scales are particular for the particular species, such as about 1 minute for molecular fouling, about hours to weeks for microfouling (e.g., about 1-24 hours for bacteria and about 1 week for microalgae or fungi), and about 2-3 weeks for macrofouling (e.g., by macroalgae or invertebrates). Regarding length scales, biofouling occurs as a function of the penetration depth of the surface. For instance, biofouling generally occurs first as a conditioning film for molecular fouling; then, the deposition of bacteria, microalgae, and fungi for microfouling; and, next, the deposition of macroalgae and invertebrates for macrofouling. In some embodiments, the coating of the invention includes control of biofouling on any of these time and/or length scales (e.g., on marine surfaces).

Finally, the present invention can be useful to control biofouling from any source. Exemplary sources include microorganisms (e.g., bacteria, algal spores, single cell diatoms, barnacle cyprids, tubeworms, parasites, and marine fungi), plants, algae, cells (e.g., mammalian cells, such as endothelial cells or red blood cells), animals, as well as extracellular proteins (e.g., polysaccharides or fibronectin) or metabolites of any of these organisms.

EXAMPLES

Example 1: Onium-Based Polymeric Biocide

Polymeric biocides comprise a class of polymers with antimicrobial activity that inhibits the growth of microorganisms. Typically, polymeric biocides are produced by attaching an active antimicrobial agent onto a polymer backbone via an alkyl or acetyl linker. Generally, polymeric biocides enhance the antimicrobial activity of the small molecule agent, yet are nonvolatile and chemically stable, decreasing environmental concerns. Polymeric biocides typically kill bacteria by first adsorbing onto the bacterial cell wall. Since most bacterial surfaces are negatively charged, adsorption is typically most effective with cationic biocides.

The antimicrobial agent then diffuses through the cell wall and is adsorbed onto the cytoplasmic membrane. The disruption of the cytoplasmic membrane and subsequent leakage of the cytoplasm leads to death of the cell. The antimicrobial activity can be affected by the molecular weight of the polymer, the structure of the counter anion associated with the polymer, and the spacer length of the alkyl chain. See Kanazawa A et al., "Antibacterial activity of polymeric sulfonium salts," *J. Poly. Sci. A* 1993; 31:2873-6; and Kanazawa A et al., "Novel polycationic biocides: synthesis and antibacterial activity of polymeric phosphonium salts," *J. Poly. Sci. A* 1993; 31:335-43.

Ideally, an antifouling polymer should be easily and inexpensively synthesized, be stable in long-term storage and usage, be insoluble in water to prevent toxicity issues, not decompose or emit toxic products, be regenerated upon loss of activity, and/or have a high antimicrobial activity toward biofouling microorganisms. Kanazawa et al. have investigated the antibacterial activity of both phosphonium- and sulfonium-based polymeric biocides. They found that these polymeric biocides exhibit high antibacterial activity and that the high positive charge of the polycations favored adsorption to and diffusion into the negative cell membrane. See Kanazawa A et al., "Antibacterial activity of polymeric sulfonium salts," *J. Poly. Sci. A* 1993; 31:2873-6; and Kanazawa A et al., "Novel polycationic biocides: synthesis and antibacterial activity of polymeric phosphonium salts," *J. Poly. Sci. A* 1993; 31:335-43.

The present invention is directed to an onium-based polymer that has similar antimicrobial and antibacterial properties to quaternary ammonium salts, as the mode of biocidal action can be similar to the mode of action of the ammonium salts. For example, the onium-based polymer can comprise a sulfonium-based polymer. Polymeric sulfonium salts can provide a biocide by tethering to a coating surface where the alkyl side chain acts as a biocide.

Figure 3A:
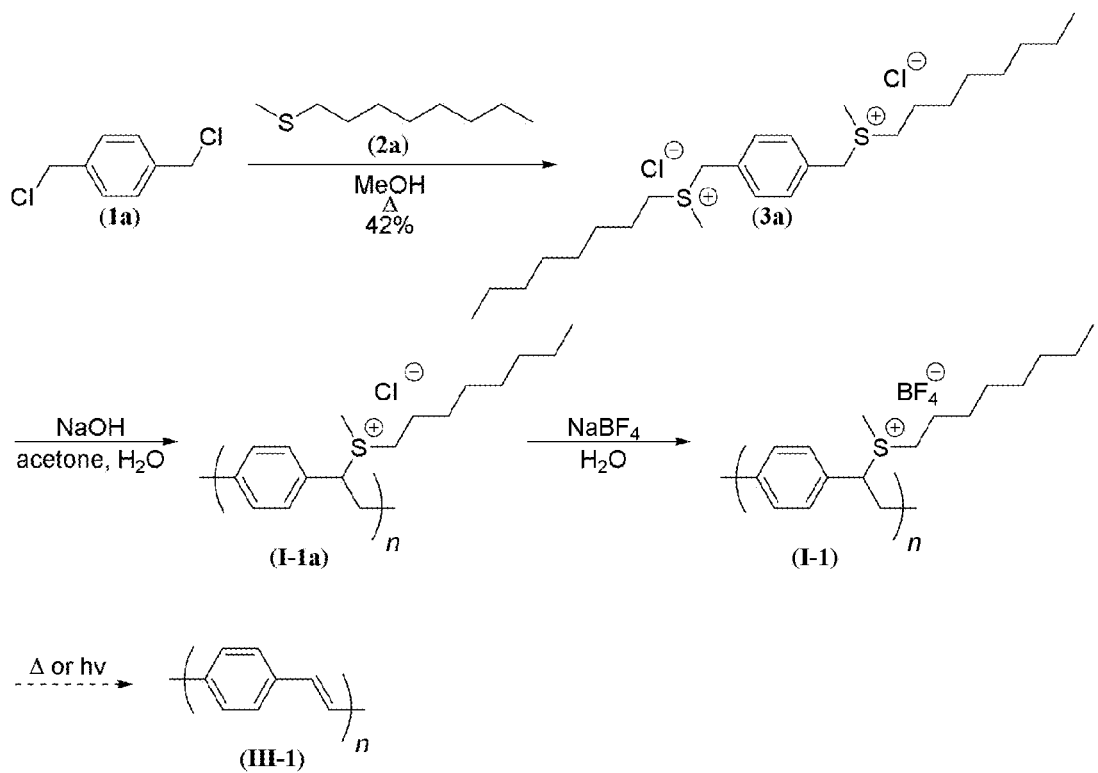
FIG. 3A-3C shows (A) a synthetic scheme for PPV-based polymer (I-1); (B) graphs showing the switching characteristics of this polymer; and (C) a synthetic scheme for PPV-based polymer (I-2).

As shown in FIG. 3A, the sulfonium is linked at the benzylic position of a poly(phenylene ethylene) polymer (I-1). This type polymer can be transformed to a conjugated polymer eliminating thioether using heat or UV light, resulting in p-phenylene vinylene (PPV) (III-1). See Johnson R S et al., "Photopatterning poly(p-phenylenevinylene) from xanthate precursor polymers," *Chem. Commun. (Camb.)* 2011 Apr. 7; 47(13):3936-8; and Johnson R S et al., "Thermally induced failure of polymer dielectrics," *Adv. Mater.* 2010 April; 22(15):1750-3.

The polymeric sulfonium is therefore thermally and/or photochemically switchable. The structural change also leads to a decrease in adhesion. Therefore, coatings prepared using this polymer can have a releasable aspect to them. As shown in FIG. 1A, as the conjugated polymer forms upon heat or light activation the attached biofilm 12 can be detached and lifted away 14 from the surface 10.

Returning now to FIG. 3A, the synthesis of an exemplary sulfonium-based polymer biocide (I-1) starts by reacting α,α'-dichloro-p-xylene (1a) with methyloctylsulfide (2a) in a solvent (e.g., methanol or acetone) to yield monomer (3a) in reasonable yield (e.g., about 40%-50%). When the polymerization is conducted in chloroform, the yield can be much lower at only 20%. The reaction can proceed by first polymerizing the monomer (3a) to form a polymer (I-1a) and then subsequently performing the anion exchange reaction to form polymer (I-1).

Alternatively, the monomer (e.g., monomer 3a) can be subjected to an anion exchange reaction using sodium tetrafluoroborate in water to produce a sulfonium monomer having anion $BF_4^-$, and then polymerization of the monomer can be accomplished (e.g., using sodium hydroxide in a wet acetone solution). After a short time, the solution becomes viscous indicating polymerization is taking place forming a polymer. Other onium-based polymer biocides can also be used, such as diazonium-, halonium-, or phosphonium-based biocides.

Isolated and purified polymer (I-1) can be dissolved in a solvent (e.g., acetone), spray-deposited, or dip-coated onto a surface, and then dried. Upon solvent evaporation, the coating can be used as an antifouling coating. Since the active sulfonium group is a great leaving group, the polymer can be photochemically or thermally converted to a conjugated PPV (III-1), thereby eliminating a thioether (e.g., as a portion of the fouling release layer) and transforming the poly(phenylene ethylene) to p-phenylene vinylene (PPV) (e.g., thereby forming the conjugated, polymerized layer). In the process of conversion, the contact angle of the surface will change as well as the volume of the polymer. This change in contact angle and volume can be used to "pop-off" the attached biofilm.

Figure 4A:
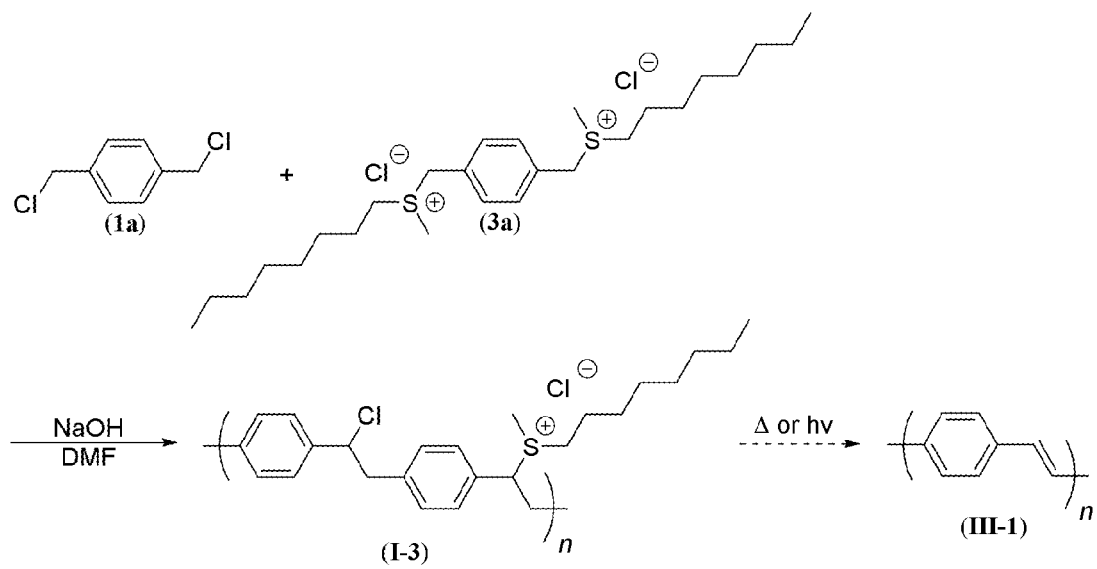
FIG. 4A-4B shows synthetic schemes for PPV-based copolymers. Provided are schemes for (A) copolymer I-3 and (B) copolymer (I-4).

Preferably, the sulfonium-based polymeric biocide is insoluble in water to prevent toxicity issues and provide an extended life of the antibiofouling coating. FIG. 4A shows a synthesis of a sulfonium-based copolymer biocide to reduce water solubility. Specifically, FIG. 4A describes the synthesis of copolymer (I-3) by reacting α,α'-dichloro-p-xylene (1a) with phenylene ethylene-2-methyl, dioctyl sulfonium dichloride (3a).

Example 2: Synthesis of PPV-Based Polymers

PPV-based polymers and copolymers were synthesized having either sulfonium or ammonium cation groups.

Sulfonium PPV-based polymer (I-1) was synthesized as provided in FIG. 3A. In brief, α,α'-dichloro-p-xylene (1a) was reacted with methyloctylsulfide (2a) to provide the sulfonium precursor (3a). This precursor (3a) was polymerized to form polymer (I-1a), which was then reacted with $NaBF_4$ for an anion exchange reaction that formed polymer (I-1). As can be seen, switching of polymer (I-1) provides conjugated PPV polymer (III-1).

Figure 3B:
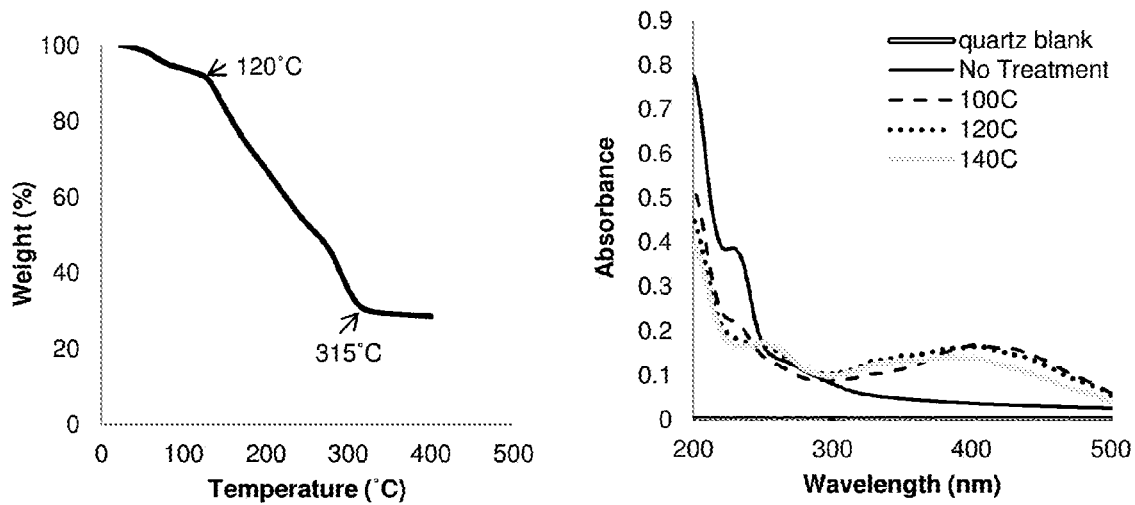

Thermal exposure resulted in elimination of the cation group and formation of conjugated polymer (III-1). As shown in FIG. 3B, thermogravimetric analyses showed that polymer (I-1) displayed about 65% weight loss upon exposure to temperatures between 120° C. and 315° C. (FIG. 3B, left). UV-Vis spectroscopy also confirmed thermal elimination at about 120° C. (FIG. 3B, right).

Figure 3C:
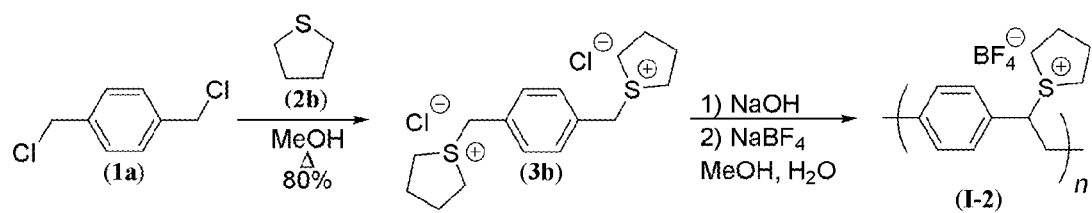

The polymer can have any useful cation. For instance, sulfonium PPV-based polymer (I-2) includes a cyclic sulfonium group to reduce water solubility. As shown in FIG. 3C, synthesis of this polymer includes use of a cyclic sulfide agent (2b) to provide monomer (3b), which can be polymerized and treated with the appropriate anion source to provide polymer (I-2).

Figure 4B:
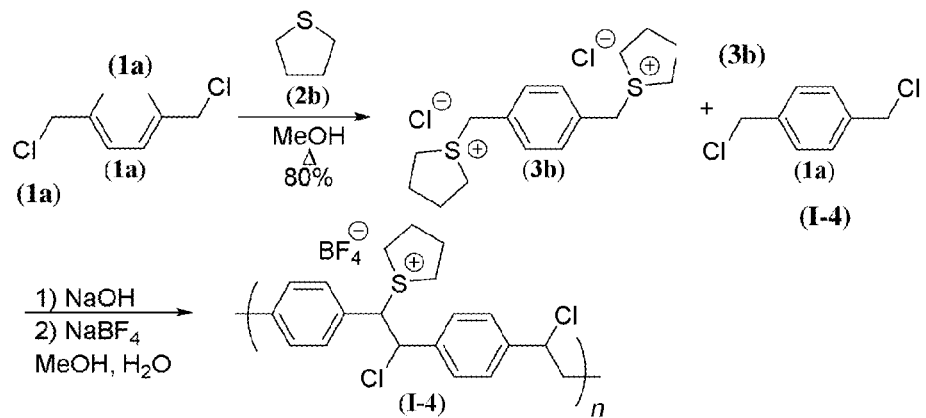

The polymer of the invention also includes copolymers. For instance, as shown in FIG. 4A, copolymer (I-3) can be formed by reacting sulfonium monomer (3a) with phenyl monomer (1a). Copolymers can include cyclic cation groups. For instance, as shown in FIG. 4B, copolymer (I-4) can be formed by reacting cyclic sulfonium monomer (3b) with phenyl monomer (1a). The present invention encompasses modified versions of PPV-based polymers, which can be obtained by optimizing any of the polymers herein by including one or more substituents on the backbone or employing other onium cations (e.g., any described herein).

Example 3: Synthesis of Siloxane-Based Polymers

The polymers of the invention also include those having different polymeric backbones. For instance, siloxane-based polymers and copolymers were synthesized having either sulfonium or ammonium cation groups. As shown in FIG. 5A, prior to switching, the siloxane-based polymer includes an onium group $B^+$ that is attached to the backbone by a linker $X^L$. After switching, the onium group $B^+$ is released, and the resultant linker $X^{L'}$ has a conjugated bond arising from the elimination of B. Specific, non-limiting examples of switched polymer having a resultant linker with a conjugated bond include polymers (IV-1) and (IV-3) (FIGS. 6A and 6B).

Ammonium siloxane-based copolymer (II-3) was synthesized as provided in FIG. 6A. In brief, 3-chloropropylmethyldimethoxysilane (5a) was reacted with an iodination agent (e.g., NaI or LiI) to provide 3-iodopropylmethyldimethoxysilane (5b). This iodinated compound (5b) was reacted with siloxane monomer (7a) in the presence of a Nafion® catalyst in water to form polymer (8a). Then, polymer (8a) was reacted with triethylamine in acetonitrile to form cationic copolymer (II-3a). Subsequent oxidation with $AgO_2$ provided cationic copolymer (II-3) having a hydroxide anion. As can be seen, switching of polymer (II-3) provides conjugated siloxane copolymer (IV-3).

Polymer versions including only one type of monomer can also be formed. For instance, as provided in FIG. 6B, the iodinated monomer (5b) can be polymerized to form polymer (6a), which can be subsequently reacted with an onium precursor agent (e.g., triethylamine, methyloctylsulfide, or any described herein) to form cationic polymer (II-Ca) (e.g., where R is an onium cation, such as a sulfonium, ammonium, diazonium, halonium, or phosphonium cation). After anion exchange, the resultant cationic polymer (II-Cb) was formed. As can be seen, switching of polymer (II-Cb) provides conjugated siloxane polymer (IV-1).

Figure 6C:
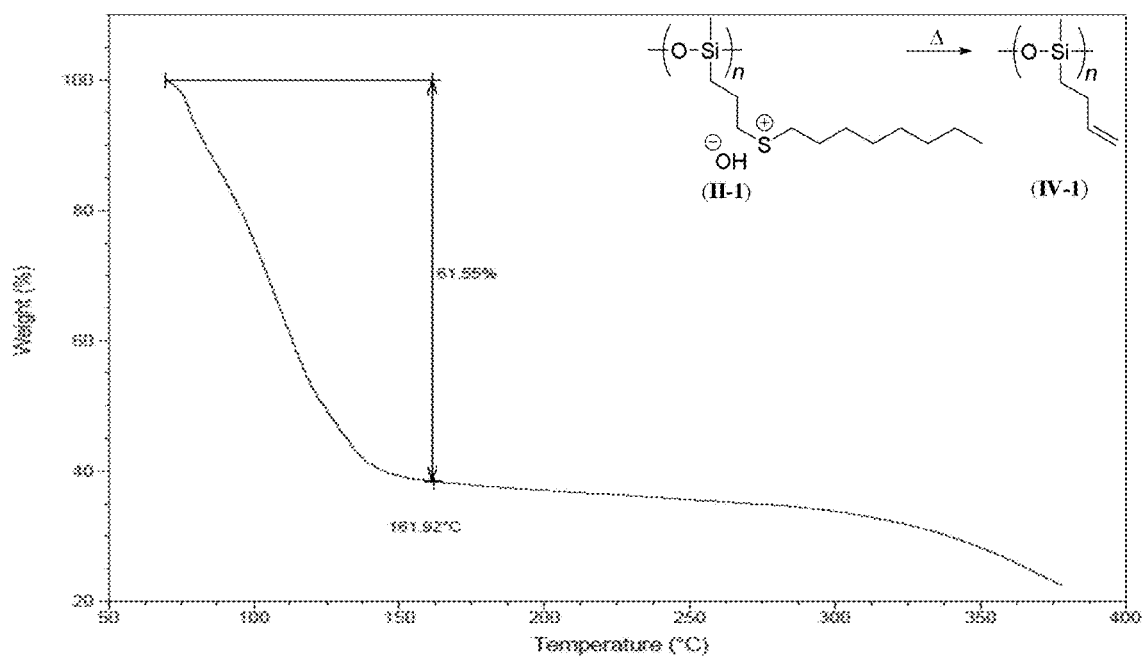
Figure 6D:
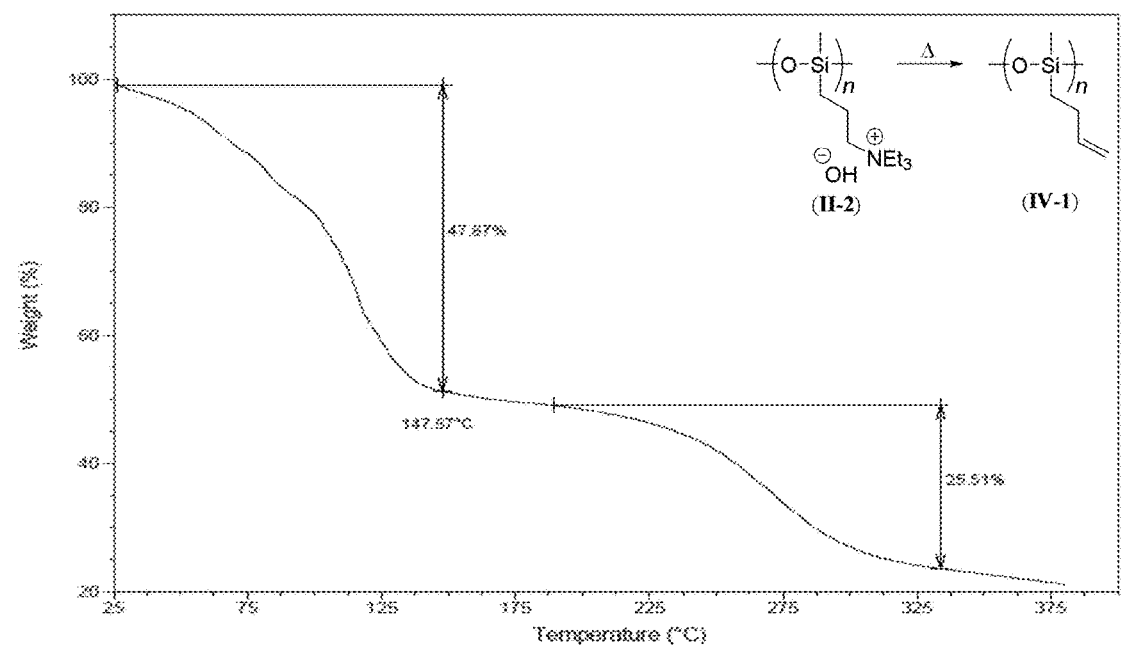

Siloxane-based polymers (II-1) and (II-2) were characterized by X-ray photoelectron spectroscopy (XPS), TGA, and infrared spectroscopy. Table 1 shows the results of XPS analysis of these polymers, which were heat treated for 30 minutes at 150° degrees and then analyzed for salt loss. Also provided are TGA analyses of the sulfonium polymer (II-1) and the ammonium polymer (II-2) (FIG. 6C-6D). As can be seen, additional siloxane-based polymers having modified backbones or onium cations can be optimized and tested with the conditions and methods described herein.

TABLE 1

XPS analysis of polymers (II-1) and (II-2)

| Coating | XPS Analysis - Atomic Concentration [%] | | | | | | |
|---|---|---|---|---|---|---|---|
| | C | N | O | S | Si | Salt/Si | Heat treated Salt/Si |
| Sulfonium polymer (II-1) | 69 | 1 | 15 | 7 | 9 | 0.778 | 0.384 |
| Ammonium polymer (II-2) | 70 | 5 | 16 | 0 | 8 | 0.625 | 0.333 |

Example 4: Toxicity Testing of Sulfonium Cations

Figure 7:
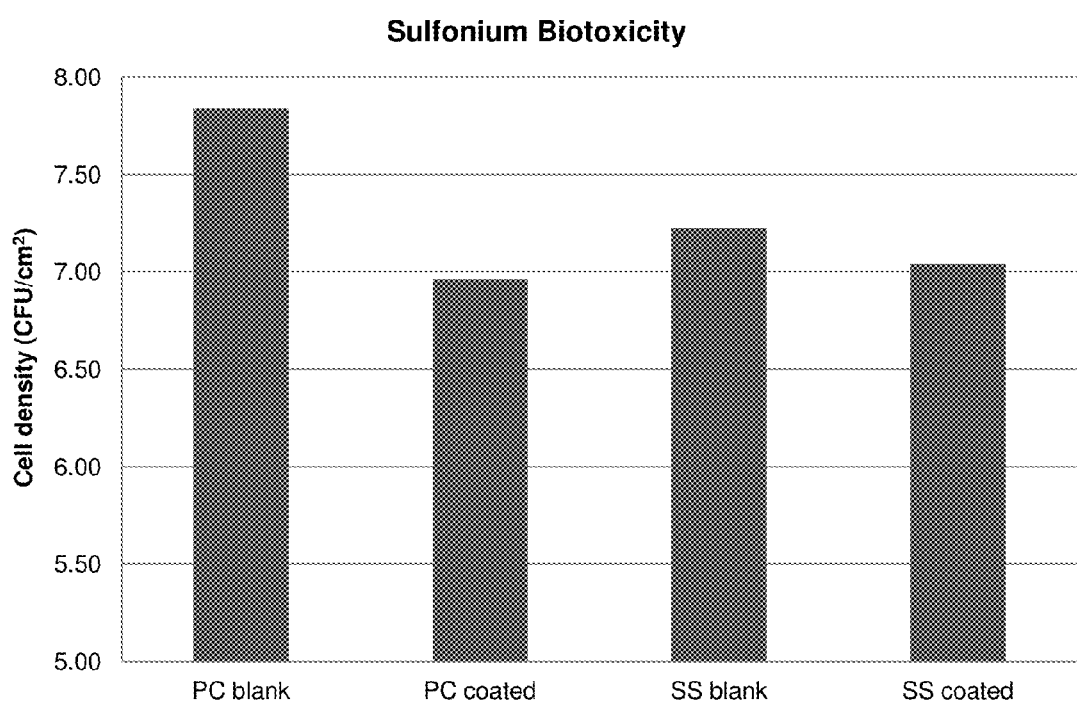
FIG. 7 is a graph showing sulfonium biotoxicity using *Pseudomonas fluorescens* with various surfaces, including a control polycarbonate surface (labeled "PC blank"), a coated polycarbonate surface (labeled "PC coated"), a control stainless steel surface (labeled "SS blank"), and a coated stainless steel surface (labeled "SS coated"). Control surfaces were bare materials, and coated surfaces included polymer (I-1).

After switching, the coatings of the invention release one or more onium cations. The biotoxicity of one onium cation (i.e., sulfonium cations) was tested under various conditions. FIG. 7 is the result of testing done in a CDC biofilm reactor with *Pseudomonas fluorescens*. Briefly, the CDC Biofilm Reactor includes eight (8) polypropylene coupon holders suspended from a UHMW-polyethylene ported lid. The coupon holders can accommodate three ½ inch (12.7 mm) diameter coupons each. The lid with coupon holders and coupons was mounted in a 1 liter glass vessel with side-arm discharge port. Artificial sea water with bacteria was circulated through the vessel, while mixing and shear force was generated by a magnetic stir bar/vane rotated by a magnetic stir plate in an attempt to replicate a moving, marine environment. Coated coupons were removed after a time period, usually 48 to 72 hours and assayed for bacteria/biofilm growth.

Figure 8:
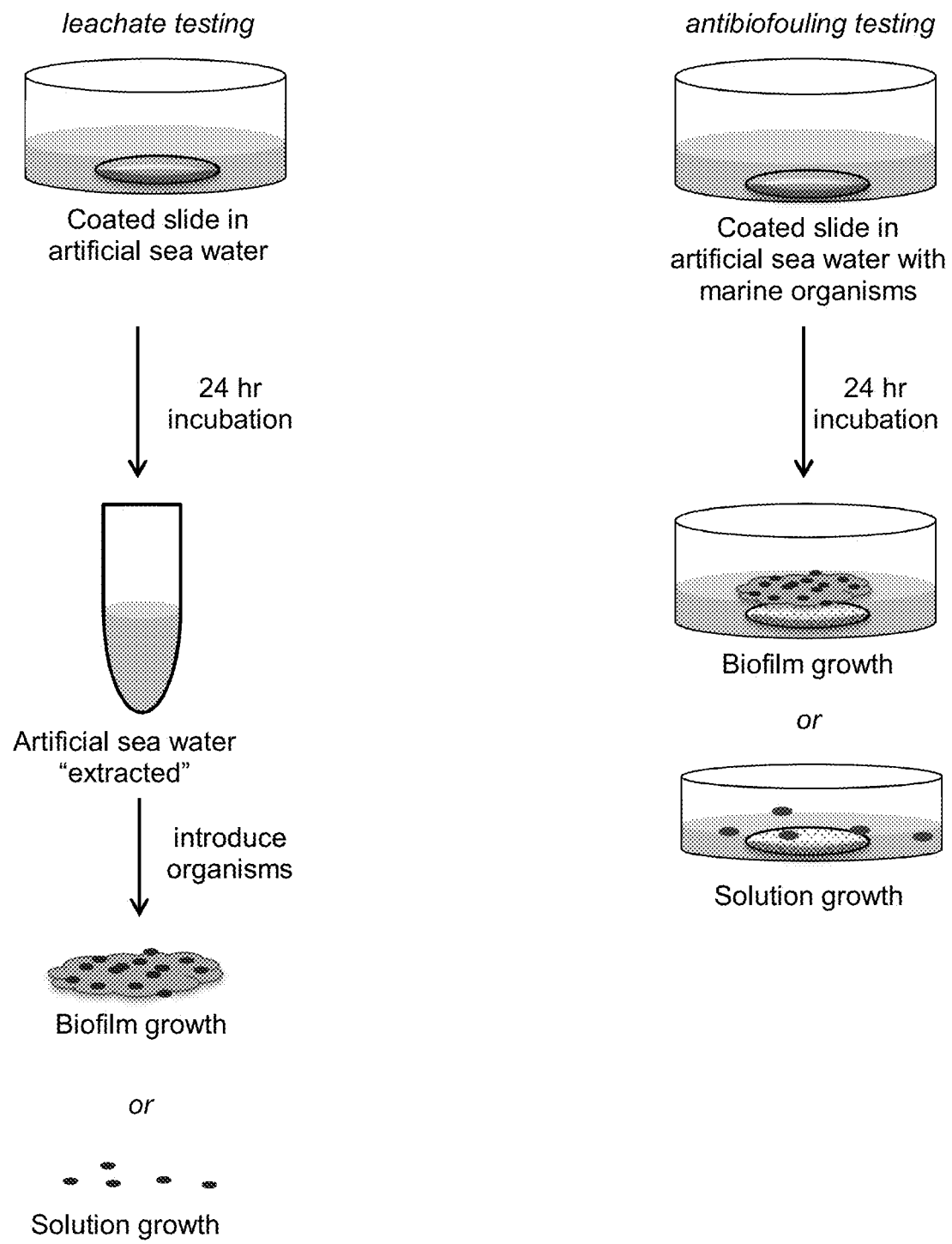
FIG. 8 is a schematic for testing various coated surfaces. Shown are schemes for leachate testing (left) and antibiofouling testing (right). As can be seen, leachate testing includes incubating the test surface in artificial sea water for 24 hours, collecting the sea water extract, and then introducing one or more marine organisms into the extract to determine whether any components within the extract affects growth and swimming behavior of the organisms. Antibiofouling testing includes incubating the test surface in artificial sea water with marine organisms for 24 hours and then characterizing biofilm growth or solution growth.

Example 5: Leachate and Antibiofouling Testing of PPV-Based Polymer (I-1) Having Sulfonium Cations The toxicity and antibiofouling properties of various coatings were tested. Leachate testing was conducted to assess the toxicity effects of the coating. As seen in FIG. 8 (left), leachate testing included incubating a coated surface in artificial sea water for about 24 hours, extracting the resultant sea water, and then introducing organisms into the sea water. The presence of organisms in solution or in a biofilm was determined using absorbance or fluorescence measurements.

Antibiofouling testing was conducted to assess the ability of the coating to resist biofilm formation. As seen in FIG. 8 (right), antibiofouling testing included incubating a coated surface in artificial sea water having one or more microorganisms. After about 24 hours, the presence of organisms in solution or in a biofilm was determined using absorbance or fluorescence measurements.

Figure 9A:
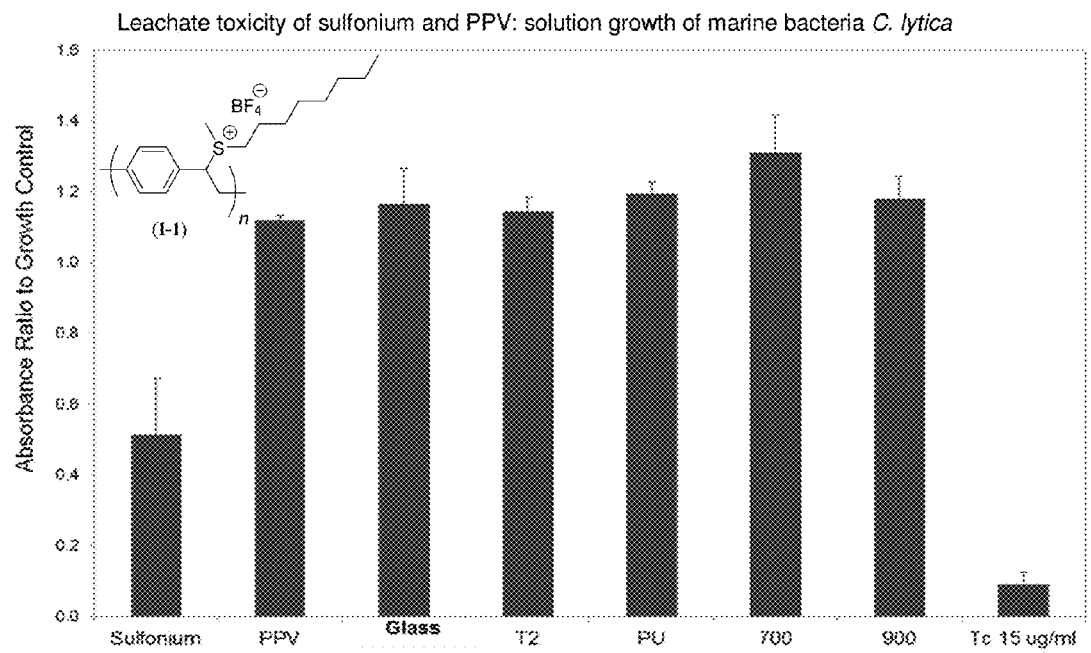
FIG. 9A-9D shows leachate and adhesion testing for PPV-based sulfonium polymer (I-1). Provided are graphs showing leachate toxicity testing to the polymer for (A) solution growth of marine bacteria *C. lytica*; (B) biofilm growth of marine bacteria *C. lytica*; and (C) growth of marine microalgae *N. incerta*. Also provided is (D) a graph showing algal cell adhesion to a surface having PPV polymer (III-1), where percent of biofilm removed is provided after spraying with a robotic water jet at 10 and 20 psi, and data are provided for the coated surface having polymer (I-1) before switching (labeled "Sulfonium") and the coated surface having polymer (III-1) after switching (labeled "PPV"). The absorbance or fluorescence is directly proportional to the amount of biofilm or solution growth. For comparison, also shown are the following controls: a glass substrate (labeled "glass"), a commercial silicone elastomer Dow Silastic® T-2 (labeled "T2"), a poly(urethane) formulation (labeled "PU"), a commercial fouling-release Intersleek® 700 formulation (labeled "700"), a commercial fouling-release Intersleek® 900 formulation (labeled "900"), and triclosan (labeled "Tc" at 15 μg/mL or 6 μg/mL). Overall, the coating provided an effective antimicrobial coating for bacteria and microalgae. As can be seen in FIG. 9D, more fouling was removed with the present coating, as compared with current commercial coatings that were shown as controls.
Figure 9B:
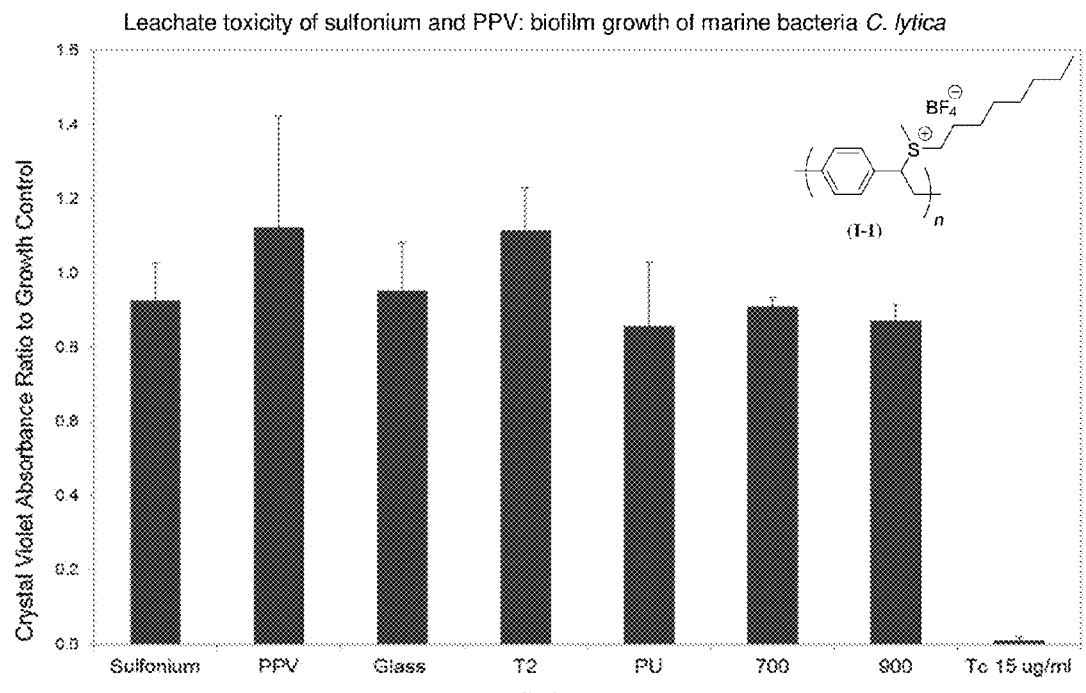
Figure 9C:
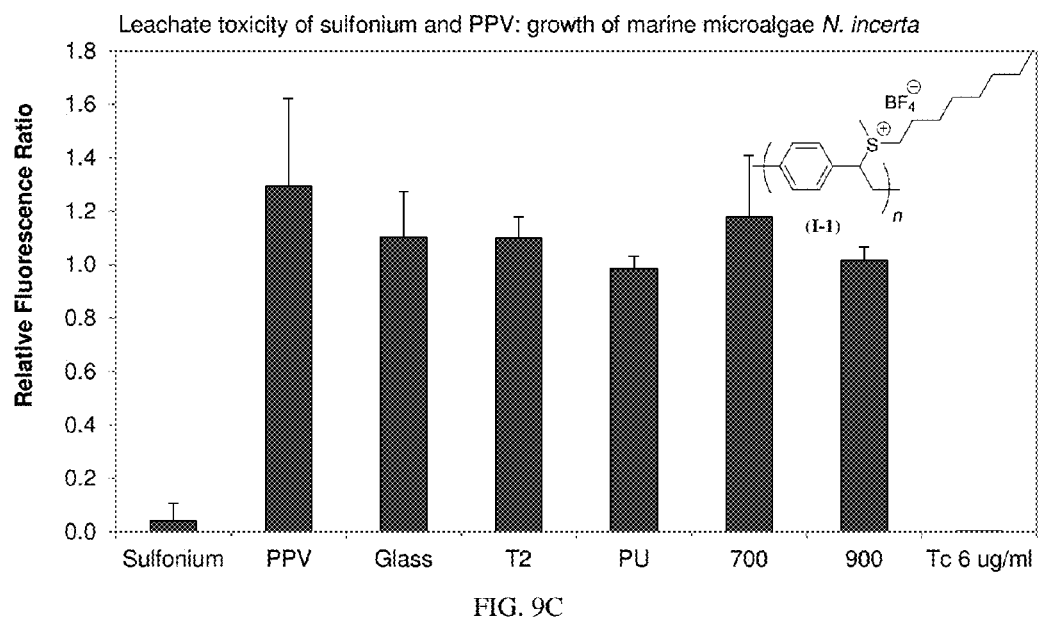

In particular, PPV-based polymer (I-1) having sulfonium cations were tested with marine bacteria *Cellulophaga lytica* (*C. lytica*) and microalgae *Navicula incerta* (*N. incerta*). As can be seen, polymer (I-1) exhibited significant marine antibacterial properties when tested for *C. lytica* in solution (labeled "Sulfonium" in FIG. 9A). However, the same polymer was not as effective for *C. lytica* in an established biofilm (labeled "Sulfonium" in FIG. 9B). Against the microalgae *N. incerta*, polymer (I-1) exhibited significant marine antifungal properties (FIG. 9C).

Without wishing to be limited by mechanism, polymer (I-1) may have exhibited this behavior because this polymer is water soluble. Accordingly, polymer (I-1) can be modified to decrease its water solubility, such as by increasing the crosslinking density of the polymer, increasing the hydrophobicity of the polymer (e.g., by increasing the alkane chain and/or providing cyclic alkane groups in the sulfonium group, by increasing hydrophobic substituents on the polymer backbone), etc. The present invention encompasses such modified polymers.

Example 6: Adhesion and Antibiofouling Testing of Conjugated PPV-Based Polymer (III-1)

We also assessed the fouling release and antibiofouling properties of a coating after switching. The tested coating included the conjugated PPV-based polymer (III-1). For example, this polymer (III-1) arises after switching a coating having polymer (I-1) or (I-2).

Figure 9D:
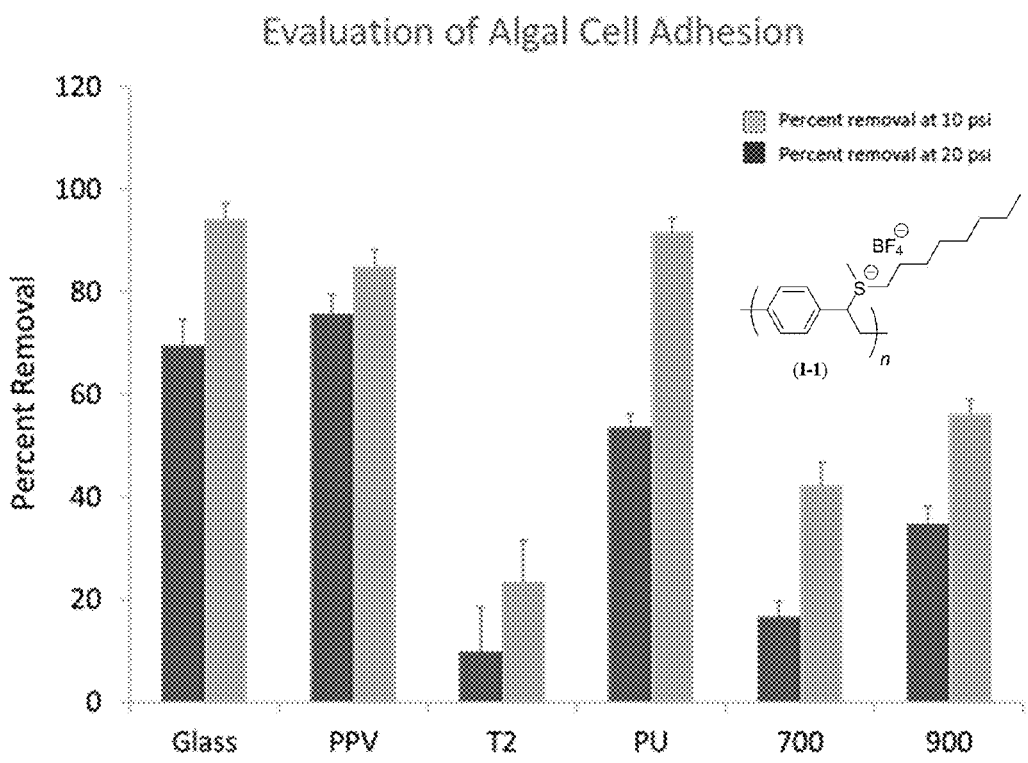

Algal cell adhesion testing was performed by incubating the microalgae on the test surface and then treating the incubated surface with a water jet at 10 psi or 20 psi. The percent removal of the microalgae was then determined. The PPV polymer provided a surface having enhanced properties. For instance, more of the fouling was removed for the PPV surface as compared to commercially available coating Intersleek® 700 and 900 (FIG. 9D, compare data labeled "PPV" versus "700" and "900").

Figure 10A:
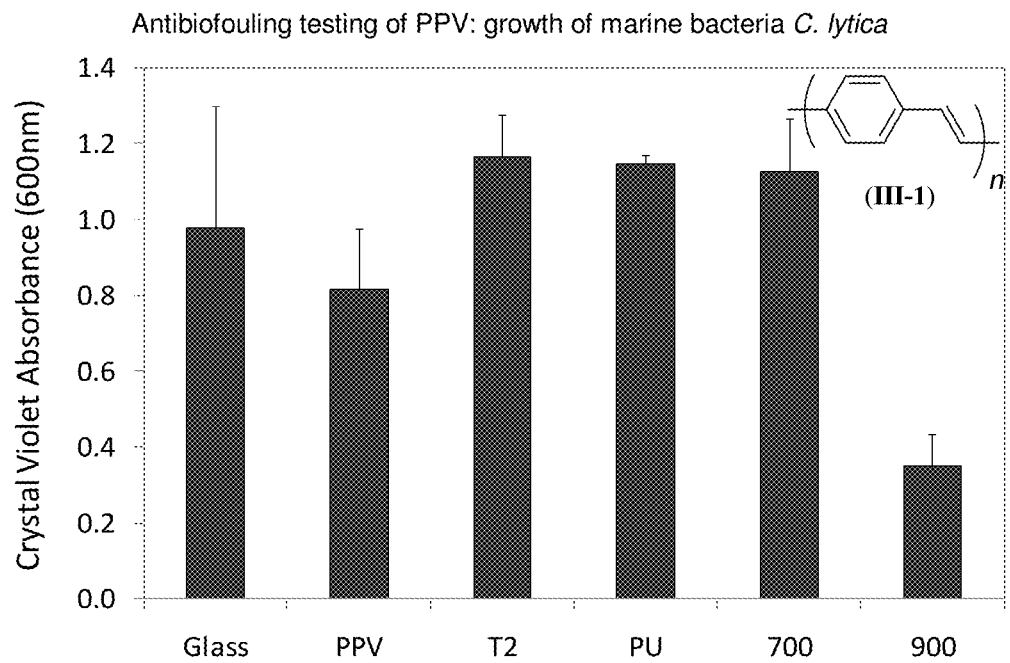
FIG. 10A-10B shows antibiofouling testing for conjugated PPV (III-1). Provided are graphs showing antibiofouling testing for growth of (A) marine bacteria *C. lytica* and (B) marine microalgae *N. incerta*. Controls are also provided (labeled "glass," "T2," "PU," "700," and "900," as explained above for FIG. 9A-9D).
Figure 10B:
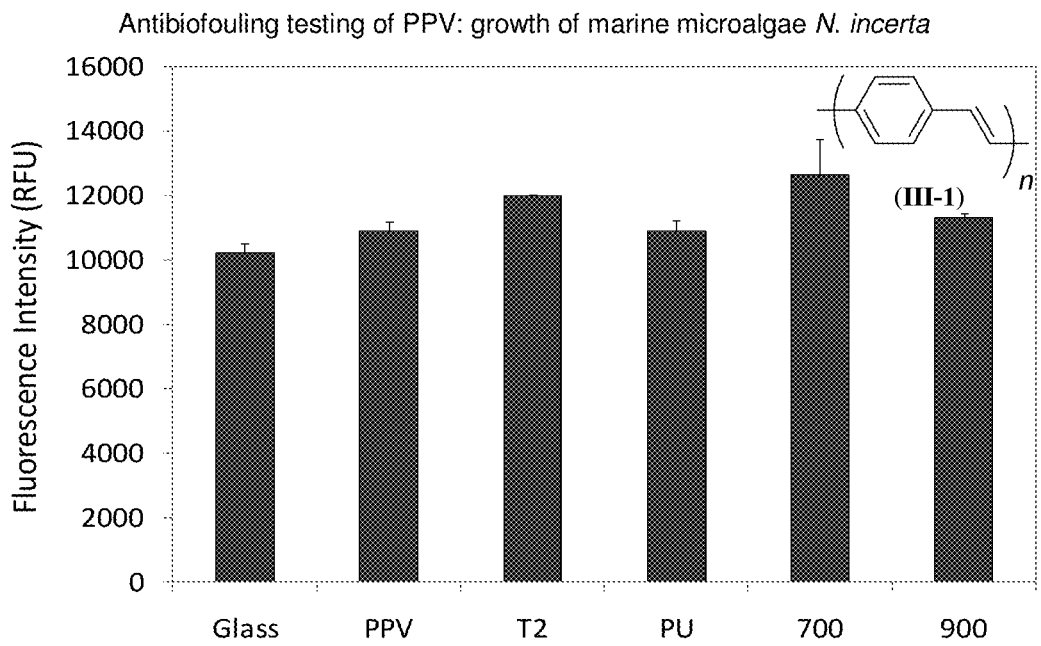

The antibiofouling properties of PPV coated slides were tested against *C. lytica* and *N. incerta*. As can be seen (FIG. 10A-10B), PPV performed better than commercially available coatings T2, PU, and 700 when tested with *C. lytica*. For *N. incerta*, PPV performed comparably with all tested commercially available coatings. Accordingly, the present invention encompasses a coating that, after switching, provides enhanced fouling release and/or antifouling properties.

Example 7: Leachate and Antibiofouling Testing of Siloxane-Based Polymer (11-3) Having Ammonium Cations The toxicity and antibiofouling properties of a siloxane-based polymer (II-3) were tested. The conditions for leachate and antibiofouling testing were as described above in Example 5 and FIG. 8.

Figure 11A:
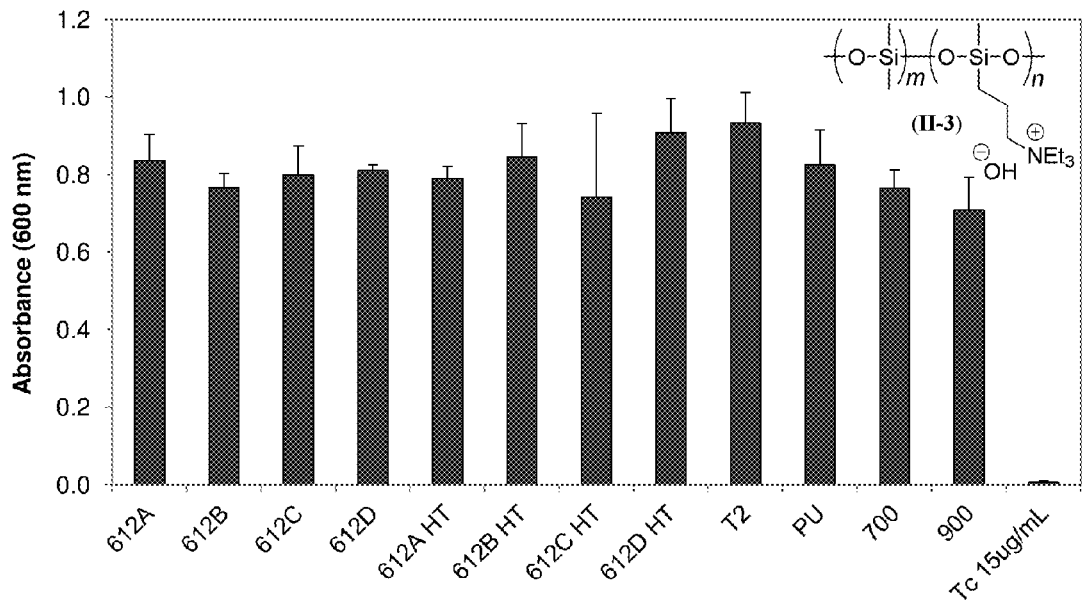
FIG. 11A-11B shows leachate testing for siloxane-based ammonium copolymer (II-3). Provided are graphs showing leachate toxicity testing to the polymer for growth of (A) marine bacteria *C. lytica* and (B) marine microalgae *N. incerta*. Tested surfaces included glass coupons with an ammonium silane polymer (i.e., copolymer (II-3) without the dimethoxydimethylsilane component) (labeled "612A"). Other surfaces included glass coupons with copolymer (II-3) having a Si to N ratio of 3:1 (labeled "612B") or a Si to N ratio of 1:4 (labeled "612C"); or copolymer (II-B) with a Si to N ratio of 1:4 (labeled "612D"). Also shown are corresponding coatings treated with heat ("HT") to form copolymer (IV-3) (labeled "612A HT," "612B HT," "612C HT," and "612D HT"). Controls are also provided (labeled "T2," "PU," "700," "900," and "Tc," as explained above for FIG. 9A-9D). As can be seen, leachate testing indicates the lack of water soluble components.
Figure 11B:
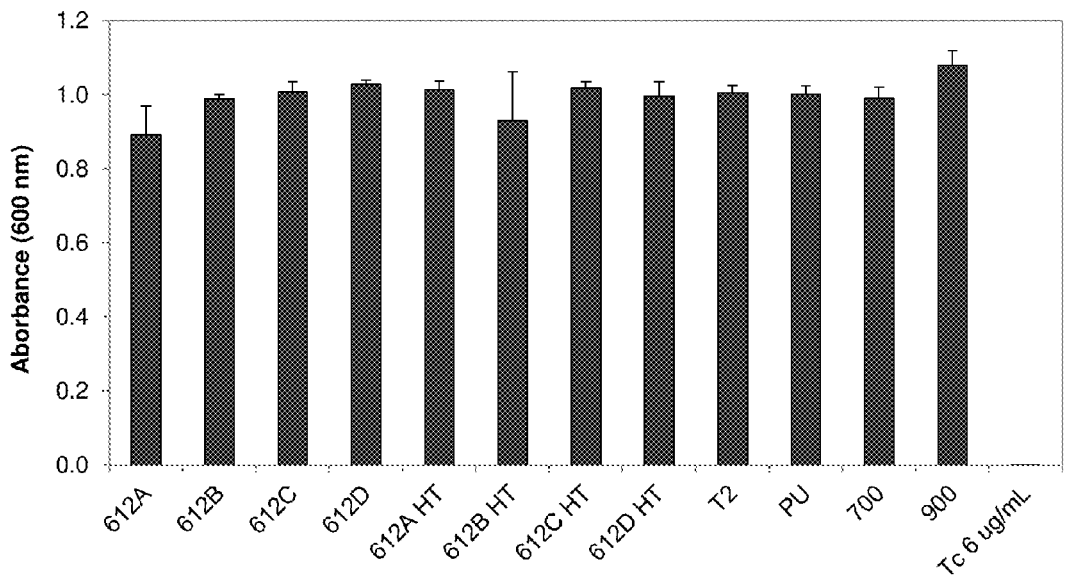
Figure 12A:
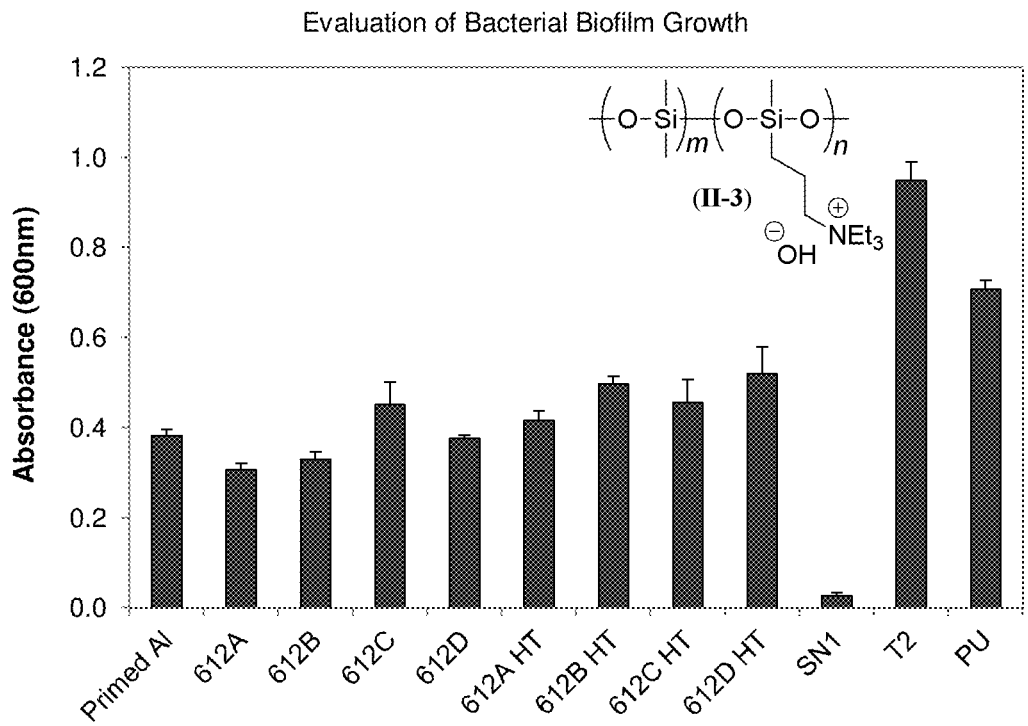
FIG. 12A-12B shows antibiofouling testing for siloxane-based ammonium copolymer (II-3) before switching. Provided are graphs showing antibiofouling testing for growth of (A) marine bacteria *C. lytica* and (B) marine microalgae *N. incerta*. Controls are also provided, including a primed aluminum surface (labeled "primed Al"); a surface including commercially available ePaint® SN-1 having biocide Sea-Nine 211®, which is 4,5-dichloro-2-n-octyl-4-isothiazolin-3-one (labeled "SN1"); as well as "T2" and "PU," which are explained above for FIG. 9A-9D. As can be seen, we observed reduction of the established bacterial biofilm with the test coating.
Figure 12B:
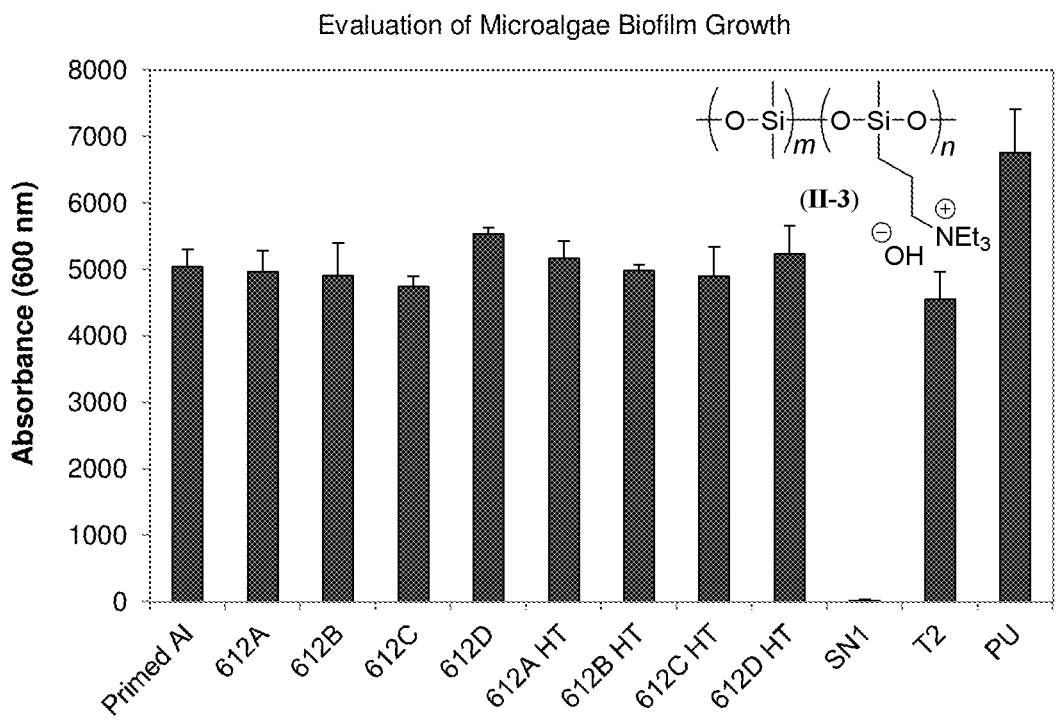

Siloxane-based polymer (II-3) was tested for its antibacterial properties with *C. lytica* and its antimicroalgal properties with *N. incerta*. As can be seen, leachate testing of polymer (II-3) performed comparably with commercially available coatings for both *C. lytica* and *N. incerta* (FIG. 11A-11B). In addition, leachate testing indicated no water solubility of the test polymer (II-3). This coating was also effective for established biofilms. For established bacterial biofilms with *C. lytica*, the coating was more effective than commercially available coatings T2 and PU (FIG. 12A). For established microalgal biofilms with *N. incerta*, the coating was as effective as commercially available coatings T2 and PU (FIG. 12B).

Example 8: Adhesion Testing of Conjugated Siloxane-Based Polymer (IV-3)

We also assessed the fouling release and antibiofouling properties of a siloxane-based coating after switching. The tested coating included the conjugated siloxane-based polymer (IV-3). For example, this polymer (IV-3) arises after switching a coating having polymer (II-3).

Figure 13A:
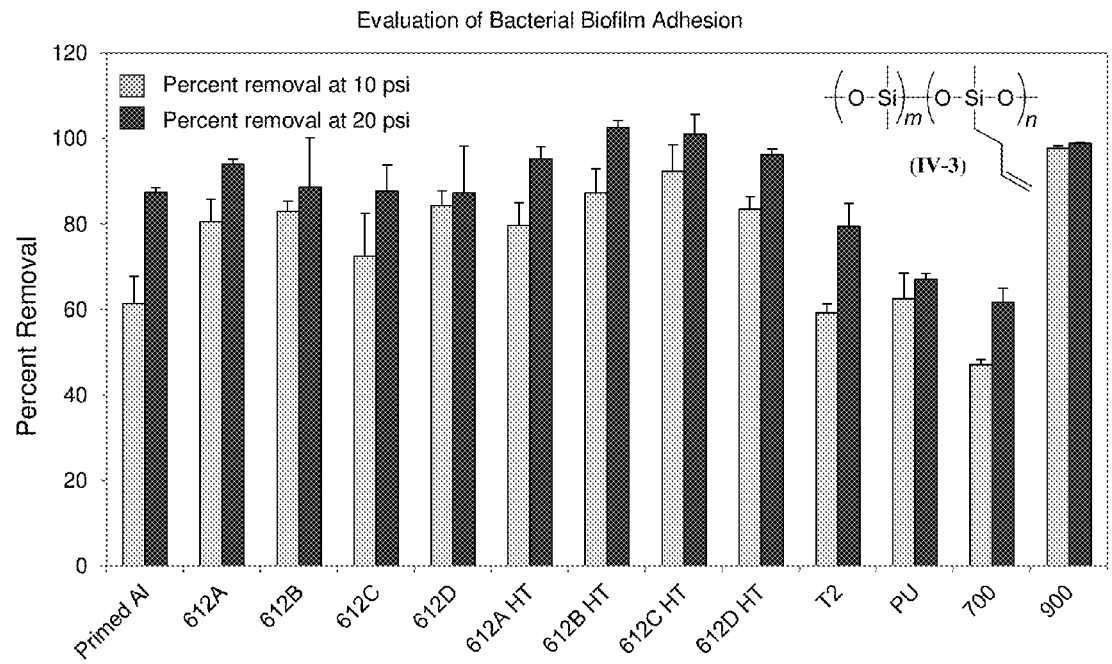
FIG. 13A-13B shows adhesion testing for a conjugated, siloxane-based copolymer (IV-3) obtained after switching cationic polymer (II-3). Provided are graphs showing antibiofouling testing for growth of (A) marine bacteria *C. lytica* and (B) marine microalgae *N. incerta*. Controls are also provided, including a primed aluminum surface (labeled "primed Al"), as well as "T2," "PU," "700," and "900," which are explained above for FIG. 9A-9D. As can be seen, the coating after switching provided effective removal of the biofilm for both bacteria and microalgae.
Figure 13B:
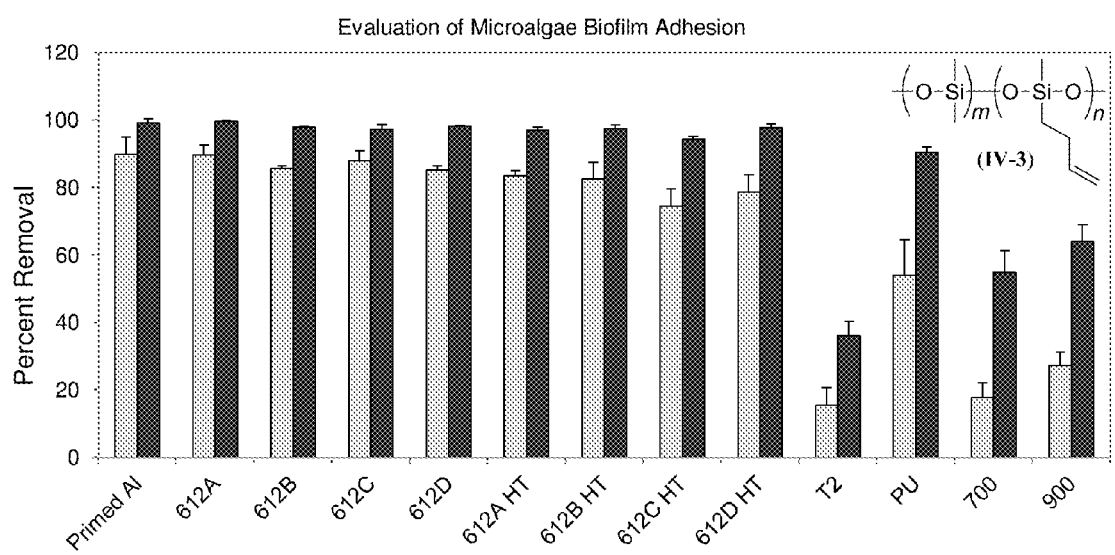
Figure 14:
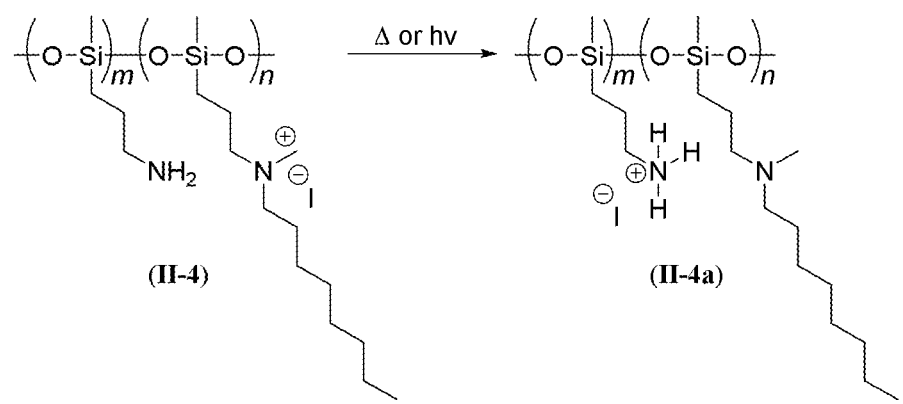
FIG. 14 shows an exemplary copolymer (II-4) after switching (II-4a). Copolymer (II-4) is the biocide, which can be thermally converted to the non-biocide version (II-4a). Whereas copolymer (II-4) contains a large alkyl group that can be inserted into cell walls and cause cell death, copolymer (II-4a) will not cause cell death via the same mechanism.

Bacterial and algal cell adhesion testing was performed by incubating the bacteria or microalgae on the test surface and then treating the incubated surface with a water jet at 10 psi or 20 psi. The percent removal of the bacteria or microalgae was then determined. The siloxane polymer provided a surface having enhanced properties. For instance, more of the fouling was removed for the siloxane surface as compared to commercially available coating Intersleek® 700 (FIG. 13A) for both bacteria and microalgae.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of treating a marine surface, the method comprising:
applying a first antifouling coating having releasable and switchable properties on the marine surface, or a portion thereof, wherein the coating comprises an onium cation covalently attached to an alpha carbon of a switchable polymer;
treating the first coating with heat or ultraviolet light to release the cation, thereby maintaining a polymerized layer on the marine surface, wherein the polymerized layer comprises a conjugated form of the switchable polymer; and
treating the polymerized layer with one or more onium cation precursors to generate a second antifouling coating on the marine surface.

2. The method of claim 1, further comprising:
performing an anion exchange reaction with the polymerized layer and an oxidizing agent or a ZA agent, in which Z is an alkali cation or an alkaline cation and A is an anion.

3. The method of claim 1, further comprising, before applying the first antifouling coating:
applying a primer layer between the marine surface and the first antifouling coating.

4. The method of claim 3, wherein the primer layer comprises a primer or a siloxane polymer.

5. The method of claim 4, wherein the primer is selected from the group consisting of an epoxy-based primer, a polyamide epoxy-based primer, a vinyl-based primer, and a zinc-based primer.

6. The method of claim 4, wherein the siloxane polymer is a trialkoxy siloxane or a trihalide siloxane.

7. The method of claim 1, wherein the switchable polymer comprises one or more hydrogens covalently attached to a beta carbon that is adjacent to the alpha carbon.

8. The method of claim 1, wherein the onium cation is a sulfonium cation, an ammonium cation, an oxonium cation, a diazonium cation, a halonium cation, or a phosphonium cation.

9. The method of claim 1, wherein the switchable polymer comprises a polyphenylene backbone or a polysiloxane backbone.

10. The method of claim 9, wherein the switchable polymer comprises a conjugated form of the polyphenylene backbone or the polysiloxane backbone.

11. The method of claim 1, wherein the switchable polymer has a structure of:

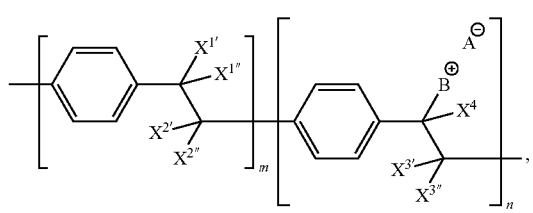

(I)

wherein:
each of $X^{1'}$, $X^{1''}$, $X^{2'}$, $X^{2''}$, $X^{3'}$, $X^{3''}$, and $X^4$ is, independently, selected from the group consisting of H, optionally substituted $C_{1-6}$ alkyl, optionally substituted $C_{2-6}$ alkenyl, and halo;
B is an onium cation;
A is an anion;
m is an integer of from 0 to 1000; and
n is an integer of from 1 to 1000.

12. The method of claim 11, wherein at least one of $X^{3'}$ and $X^3$ is H.

13. The method of claim 11, wherein m is not 0.

14. The method of claim 1, wherein the switchable polymer has a structure of:

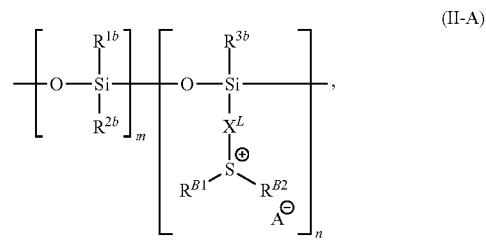

(II-A)

wherein
each of $R^{1b}$, $R^{2b}$, and $R^{3b}$ is, independently, selected from the group consisting of H, hydroxyl, optionally substituted $C_{1-6}$ alkyl, optionally substituted $C_{2-6}$ alkenyl, optionally substituted $C_{1-6}$ alkoxy, and halo;
each of $R^{B1}$ and $R^{B2}$ is, independently, H, optionally substituted $C_{1-24}$ alkyl, or optionally substituted $C_{2-6}$ alkenyl; or wherein $R^{B1}$ and $R^{B2}$, taken together with the sulfur atom to which each are attached, form an optionally substituted heterocycle; or wherein $R^{B1}$ and $R^{B2}$, taken together, comprises an optionally substituted $C_{2-12}$ alkylene or an optionally substituted $C_{2-12}$ heteroalkylene;
$X^L$ is optionally substituted $C_{1-16}$ alkylene or optionally substituted $C_{1-12}$ heteroalkylene;
A is an anion;
m is an integer of from 0 to 1000; and
n is an integer of from 1 to 1000.

15. The method of claim 1, wherein the switchable polymer has a structure of:

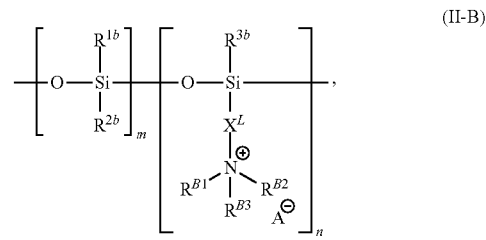

(II-B)

wherein
each of $R^{1b}$, $R^{2b}$, and $R^{3b}$ is, independently, selected from the group consisting of H, hydroxyl, optionally substituted $C_{1-6}$ alkyl, optionally substituted $C_{2-6}$ alkenyl, optionally substituted $C_{1-6}$ alkoxy, and halo;
each of $R^{B1}$, $R^{B2}$, and $R^{B3}$ is, independently, H, optionally substituted $C_{1-24}$ alkyl, or optionally substituted $C_{2-6}$ alkenyl; or wherein two or more of $R^{B1}$, $R^{B2}$, and $R^{B3}$, taken together with the nitrogen atom to which each are attached, form an optionally substituted heterocycle; or wherein $R^{B1}$ and $R^{B2}$, taken together, comprises an optionally substituted $C_{2-12}$ alkylene or an optionally substituted $C_{2-12}$ heteroalkylene;

$X^L$ is optionally substituted $C_{1-16}$ alkylene or optionally substituted $C_{1-12}$ heteroalkylene;

A is an anion; and m is an integer of from 0 to 1000; and n is an integer of from 1 to 1000.

16. The method of claim 1, wherein the switchable polymer has a structure of:

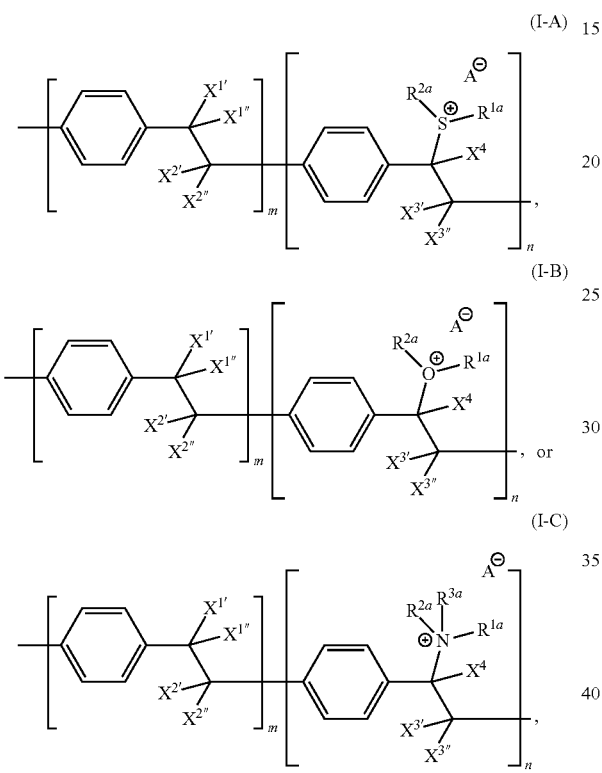

wherein:
each of $X^{1'}$, $X^{1''}$, $X^{2'}$, $X^{2''}$, $X^{3'}$, $X^{3''}$, and $X^4$ is, independently, selected from the group consisting of H, optionally substituted $C_{1-6}$ alkyl, optionally substituted $C_{2-6}$ alkenyl, and halo;

A is an anion;

each of $R^{1a}$, $R^{2a}$, and $R^{3a}$, if present, is, independently, H, optionally substituted $C_{1-24}$ alkyl, or optionally substituted $C_{2-24}$ alkenyl; or wherein two of $R^{1a}$, $R^{2a}$, and $R^{3a}$, taken together with the heteroatom to which each are attached, form an optionally substituted heterocycle; or wherein $R^{1a}$ and $R^{2a}$, taken together, includes an optionally substituted $C_{2-12}$ alkylene or an optionally substituted $C_{2-12}$ heteroalkylene, m is an integer of from 0 to 1000; and n is an integer of from 1 to 1000.

17. A method of treating a marine surface, the method comprising:
applying a first antifouling coating having releasable and switchable properties on the marine surface, or a portion thereof, wherein the coating comprises an onium cation covalently attached to an alpha carbon of a switchable polymer; and treating the first coating with heat or ultraviolet light to release the cation, thereby maintaining a polymerized layer on the marine surface, wherein the polymerized layer comprises a conjugated form of the switchable polymer, wherein the switchable polymer has a structure of:

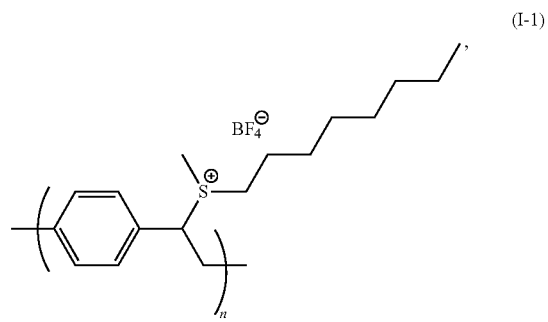

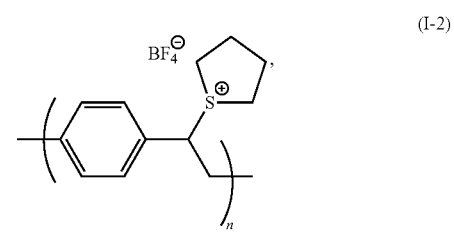

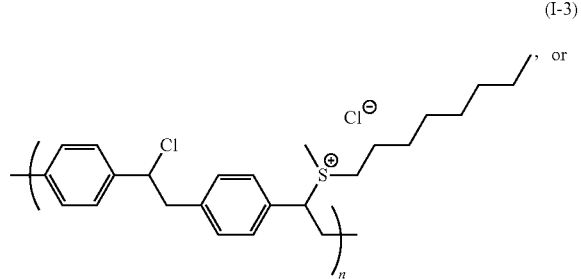

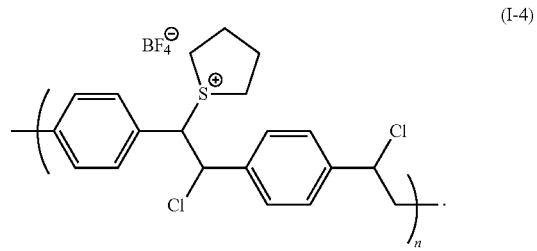

and wherein n is an integer of from 1 to 1000.

18. The method of claim 1, wherein the switchable polymer has a structure of:

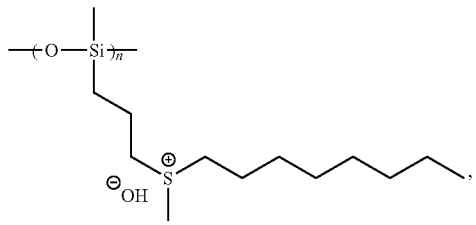 (II-1)

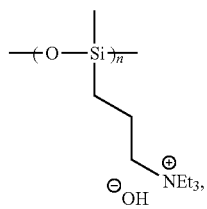 (II-2)

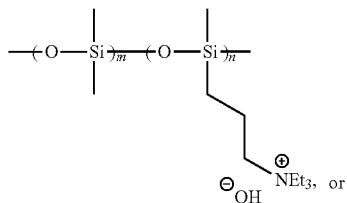 (II-3)

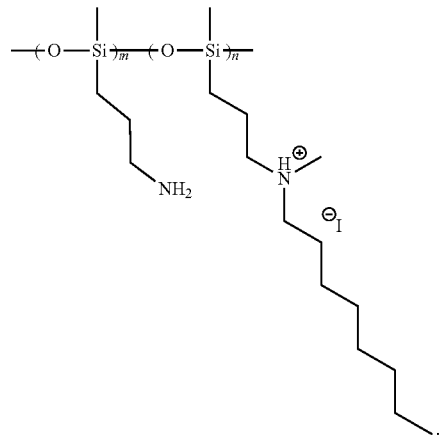 (II-4)

19. A method of treating a marine surface, the method comprising:
applying a primer layer to the marine surface;
applying a first antifouling coating having releasable and switchable properties on the primer layer, or a portion thereof, wherein the coating comprises an onium cation covalently attached to an alpha carbon of a polymer;
treating the first coating with heat or ultraviolet light to release the cation, thereby maintaining a polymerized layer on the marine surface, wherein the polymerized layer comprises a conjugated form of the polymer; and
treating the polymerized layer with one or more onium cation precursors to generate a second antifouling coating on the marine surface.

20. The method of claim 19, further comprising:
performing an anion exchange reaction with the polymerized layer and an oxidizing agent or a ZA agent, in which Z is an alkali cation or an alkaline cation and A is an anion.

* * * * *